(12) United States Patent
Doudna et al.

(10) Patent No.: US 12,270,027 B2
(45) Date of Patent: *Apr. 8, 2025

(54) METHODS AND KITS FOR IDENTIFYING CANCER TREATMENT TARGETS

(71) Applicant: The Regents of the University of California, Oakland, CA (US)

(72) Inventors: Jennifer A. Doudna, Berkeley, CA (US); Chun-Hao Huang, Berkeley, CA (US); Spencer C. Knight, Berkeley, CA (US); Nami Saghaei, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/104,640

(22) Filed: Feb. 1, 2023

(65) Prior Publication Data

US 2024/0209352 A1     Jun. 27, 2024

Related U.S. Application Data

(63) Continuation of application No. 17/717,594, filed on Apr. 11, 2022, now Pat. No. 11,584,930, which is a continuation of application No. 17/284,660, filed as application No. PCT/US2019/058853 on Oct. 30, 2019.

(60) Provisional application No. 62/753,631, filed on Oct. 31, 2018.

(51) Int. Cl.
| | |
|---|---|
| C12N 15/10 | (2006.01) |
| C12N 9/22 | (2006.01) |
| C12N 15/11 | (2006.01) |
| C12N 15/90 | (2006.01) |
| G16B 30/10 | (2019.01) |
| G16B 40/00 | (2019.01) |

(52) U.S. Cl.
CPC ........... *C12N 15/1079* (2013.01); *C12N 9/22* (2013.01); *C12N 15/11* (2013.01); *C12N 15/907* (2013.01); *G16B 30/10* (2019.02); *G16B 40/00* (2019.02); *C12N 2310/20* (2017.05); *C12N 2320/10* (2013.01); *C12N 2800/80* (2013.01)

(58) Field of Classification Search
None
See application file for complete search history.

(56) References Cited

U.S. PATENT DOCUMENTS

| | | |
|---|---|---|
| 2017/0204407 A1 | 7/2017 | Gilbert et al. |
| 2017/0260584 A1 | 9/2017 | Zheng et al. |
| 2018/0100201 A1 | 4/2018 | Garraway et al. |
| 2018/0156800 A1 | 6/2018 | Lin et al. |
| 2018/0166170 A1 | 6/2018 | Theofilatos et al. |
| 2019/0218276 A1* | 7/2019 | Regev .................... C12Q 1/686 |

FOREIGN PATENT DOCUMENTS

| | | | |
|---|---|---|---|
| CN | 106399377 A | 2/2017 | |
| WO | WO 2017/075294 | 5/2017 | |
| WO | WO 2017/083766 | 5/2017 | |
| WO | WO-2017075294 A1 * | 5/2017 | ......... C12N 15/1075 |
| WO | WO 2018/112423 | 6/2018 | |

OTHER PUBLICATIONS

Jabeen et al., "Machine Learning-Based State-of-the-Art Methods", Springer International Publishing AG 2018, N. Dey et al. (eds.), Classification in BioApps, Lecture Notes in Computational Vision and Biomechanics 26, https://doi.org/10.1007/978-3-319-65981-76, first online Nov. 2017 (Year: 2018).*

Kostyrko et al., Identification of novel combinatorial synthetic lethal vulnerabilities in KRAS-driven lung cancer . Cancer Res (2018), 78 (13. Supplement): Abstract 4362 (Year: 2018).*

Cowley, et al.; "Parallel genome-scale loss of function screens in 216 cancer cell lines for the identification of context-specific genetic dependencies"; Scientific Data; vol. 1, No. 1, 12 pages (Sep. 30, 2014).

Fellmann, et al.; "Cornerstones of CRISPR-Cas in drug discovery and therapy"; Nature Reviews; vol. 16, pp. 89-100 (Feb. 2017).

Hart, et al.; "High-Resolution CRISPR Screens Reveal Fitness Genes and Genotype-Specific Cancer Liabilities"; Cell; vol. 163, pp. 1515-1526 (Dec. 3, 2015).

Hart, et al.; "Measuring error rates in genomic perturbation screens: gold standards for human functional genomics"; Molecular Systems Biology; vol. 10, 16 pages (Jul. 2014).

Jabeen, et al.; "Machine Learning-Based State-of-the-Art Methods for the Classification of RNA-Seq Data"; Classification in BioApps; ISBN 978-3-319-65981-7; Springer International Publishing AG 2018, 43 pages (2018).

Kurata, et al.; "CRISPR/Cas9 library screening for drug target discovery"; Journal of Human Genetics; vol. 63, pp. 179-186 (Nov. 2017).

Shi, et al.; "Discovery of cancer drug targets by CRISPR-Cas9 screening of protein domains"; Nature Biotechnology; vol. 33, pp. 661-667 (Jun. 2015).

Muller, et al.; "Single-Cell mRNA Sequencing in Cancer Research: Integrating the Genomic Fingerprint"; Frontiers in Genetics; vol. 8, No. 73, 10 pages (May 2017).

Bilgin et al.; "BioSig3D: High Content Screening of Three-Dimensional Cell Culture Models"; PLOS One; vol. 11, No. 3, e0148379, pp. 1-19 (Mar. 15, 2016).

(Continued)

*Primary Examiner* — Celine X Qian
*Assistant Examiner* — Catherine Konopka
(74) *Attorney, Agent, or Firm* — Bozicevic, Field & Francis LLP

(57) ABSTRACT

In one aspect, the present disclosure provides a method for identifying treatment targets relating to tumors. In another aspect, the present disclosure provides a method for identifying biomarkers and molecular features of normal and cancer cells.

25 Claims, 12 Drawing Sheets

Specification includes a Sequence Listing.

(56) References Cited

OTHER PUBLICATIONS

Kostyrko, et al.; "Abstract 4362: Identification of novel combinatorial synthetic letal vulnerabilities in KRAS-driven lung cancer"; Cancer Research; vol. 78, No. 13_Supplement, 4362 (Jul. 1, 2018).

Moore; "The impact of CRISPR-Cas9 on target identification and validation"; Drug Discovery Today; vol. 20, No. 4, pp. 450-457 (Apr. 2015).

* cited by examiner

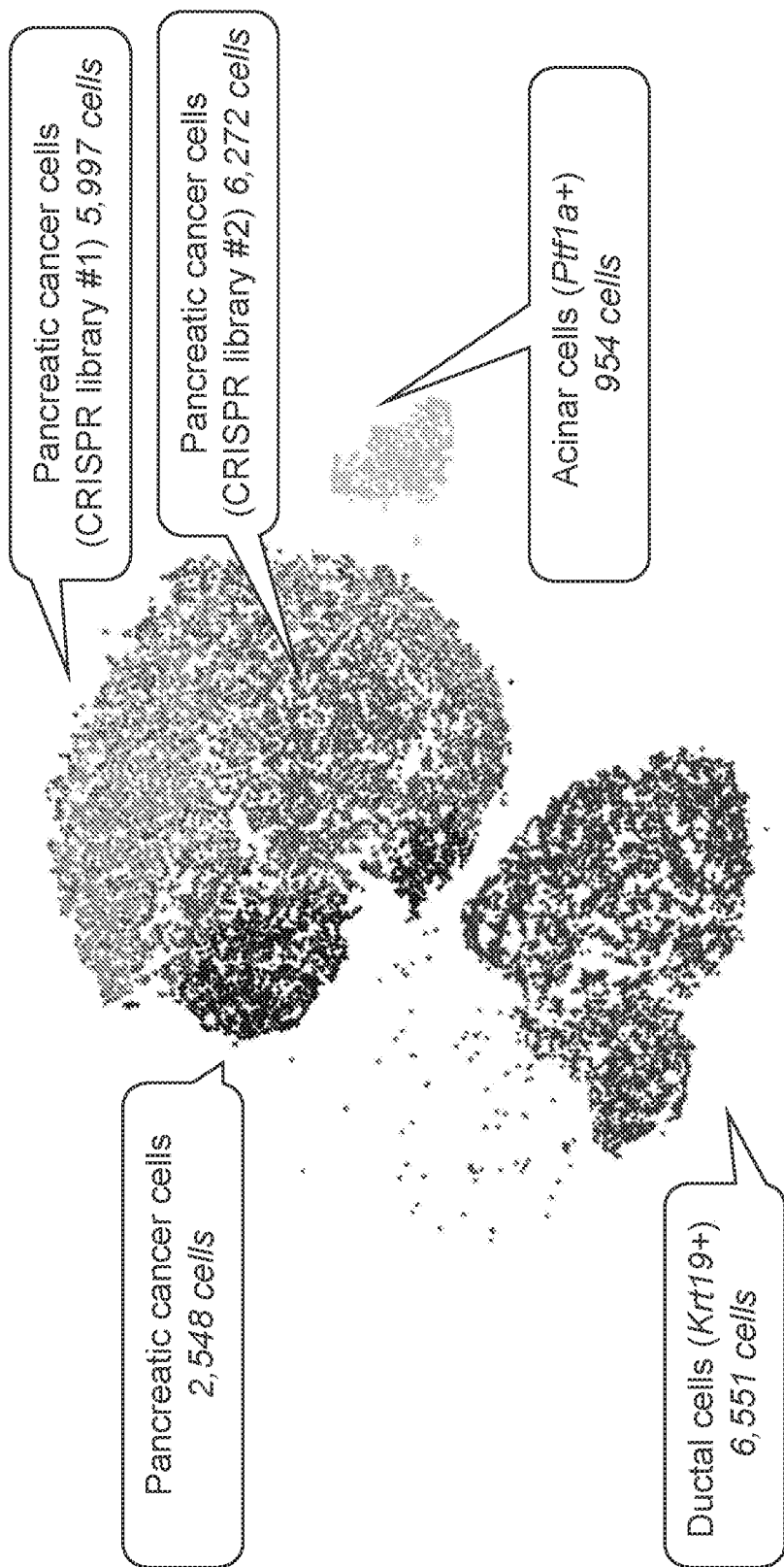

FIG. 8

| Cancer cells versus normal cells (ductal and acinar cells) | | | |
|---|---|---|---|
| *Up-regulated genes in cancer cells* | | *Down-regulated genes in cancer cells* | |
| Ddit4 | Dnajc2 | Gm10116 | Tubb2b |
| Cdkn2a | Hacd1 | Pcbd1 | Fads3 |
| Hk2 | Ddx3x | Gamt | H2-K1 |
| Hes1 | Mat2a | Gstm1 | Trp53 |
| Asns | Ddx46 | Chchd10 | Spint2 |
| Galk1 | Gm16286 | Dlk1 | Lsr |
| Shmt2 | Tpi1 | Sod3 | Prss2 |
| Cct8 | Gcat | Bst1 | Kcnk3 |
| Gars | Nmt1 | Krt7 | Vtn |
| Psph | Jun | Anxa8 | Chga |
| Ppid | Cbx3 | Slpi | Cpa1 |
| Ruvbl1 | Id3 | Sorbs2 | Tm4sf4 |
| Chchd4 | Fam3c | Ankrd1 | Gc |
| Nop16 | Pcbp4 | Msln | Reg1 |
| Eif4ebp1 | Id1 | Klra4 | Try5 |
| Gcsh | Mt2 | Igfbp7 | Ctrb1 |
| Ddx21 | Bcat1 | Gm10709 | Nts |
| Ino80e | Sparc | Tspan8 | Mdk |
| Tomm70a | Pcolce | Gjb4 | Bex2 |
| Bri3bp | Ifitm3 | Anxa3 | Nkx6-2 |
| Mpp6 | S100a4 | Krt19 | Resp18 |
| Tomm20 | Xist | Krt18 | Cldn10 |
| Nhp2l1 | Tnfrsf26 | Akap12 | Penk |
| Akr1b3 | Dusp9 | Cdc42ep5 | D930028M14R |
| Noc2l | Ly6a | Tubb2a | Cela1 |
| Nolc1 | Ccnd2 | Fbln2 | Rbp4 |
| Tomm5 | Emp3 | Cyba | Bex4 |
| Nhp2 | Prkg2 | Timp3 | Sepp1 |
| Rsl24d1 | Ndn | Ucp2 | Mest |
| Hnrnpdl | | Sgk1 | Apoe |

METHODS AND KITS FOR IDENTIFYING CANCER TREATMENT TARGETS

CROSS-REFERENCE

This application is a continuation of U.S. patent application Ser. No. 17/717,594, filed Apr. 11, 2022 and issued as U.S. Pat. No. 11,584,930 on Feb. 21, 2023, which is a continuation of U.S. patent application Ser. No. 17/284,660, filed Apr. 12, 2021, which is a U.S. National Phase Application of PCT Application No. PCT/US2019/058853, filed Oct. 30, 2019, which claims the benefit of U.S. Provisional Patent Application No. 62/753,631, filed Oct. 31, 2018, which applications are incorporated herein by reference in their entirety.

INCORPORATION BY REFERENCE OF SEQUENCE LISTING PROVIDED AS A SEQUENCE LISTING XML FILE

A Sequence Listing is provided herewith as a Sequence Listing XML, "BERK-401CON2_SEQ_LIST_March_2024.xml" created on Mar. 13, 2024 and having a size of 1,663,633 bytes. The contents of the Sequence Listing XML are incorporated by reference herein in their entirety.

INTRODUCTION

Tumorigenesis is a multistep process involving genetic alteration and gene expression deregulation in cells. Over the past few decades, targeted therapies hold hope for the treatment of many types of cancer. A common complication is that, for many patients, effective treatments are still lacking, or the drugs eventually stop working owing to the tumor heterogeneity and genetic complexity.

Studies using pharmacological-, RNAi (RNA interference)—or CRISPR (Clustered Regularly Interspaced Short Palindromic Repeats)-mediated screens have been carried out to identify targets for cancer treatment. However, many targets genes cannot be further validated in vivo due to the lack of understanding of their corresponding signaling and gene network, or because of undesired toxicities and biased selection due to overemphasis on particular phenotypes such as growth or depletion of cancer cells.

There is a need in the art for methods for identifying cancer treatment targets.

SUMMARY

In one aspect, the present disclosure provides a method for identifying treatment targets relating to tumors. The method comprises the steps of: (a) generating normal and cancer cells harboring a CRISPR/Cas effector polypeptide; (b) inhibiting expression of a target gene in the normal and cancer cells generated in step (a) by stably introducing an sgRNA expression construct directed to the target gene, thereby inhibiting expression of the target gene; (c) monitoring one or more molecular features and/or phenotypes (e.g., disease phenotypes) in the cells (e.g., by single-cell RNAseq (scRNAseq)) following inhibition of target gene expression; and (d) designating the molecular feature and disease phenotype as a target gene knockdown-related features and phenotypes (e.g., using a computer algorithm), if improvement in the molecular feature or phenotype is observed following step (b). In some cases, identification of treatment targets comprises the combinatorial interrogations of multiple genes.

In another aspect, the present disclosure provides a method for identifying biomarkers and molecular features of normal and cancer cells. The method comprises the steps of: (a) single-cell RNAseq (scRNAseq) analysis of normal and cancer cells; (b) analyzing the single-cell RNAseq on a cloud platform; (c) classifying different types of cells; (d) developing computer algorithms; and (e) identifying biomarkers and molecular features of normal and cancer cells. In some cases, the biomarkers and molecular features comprises the combinatorial expressions of multiple genes.

BRIEF DESCRIPTION OF THE DRAWINGS

FIGS. 4A-4D. Single-cell RNAseq-mediated molecular profiling of murine pancreatic cancer cells with CRISPRi libraries that functionally interrogate candidate target genes. (FIG. 4A) Based on transcript-compatibility counts, the 5,997 (biological replicate 1) and 6,272 (biological replicate 2) murine pancreatic cancer cells harboring the CRISPRi library, the parental murine pancreatic cancer cells (FIG. 2), transformed acinar cells (266-6 cells) (FIG. 2) and murine ductal cells (FIG. 2) are visualized using t-SNE and colored to label the different cell types. (FIGS. 4B-4D) Bulk analysis of the single-cell RNAseq data from the murine pancreatic cancer cells harboring the CRISPRi library, parental murine pancreatic cancer cells, transformed acinar cells (266-6 cells), and murine ductal cells. Gene ontology (GO) analysis of gene sets that were significantly upregulated or downregulated in murine pancreatic cancer cells versus acinar or ductal cells was analyzed.

FIG. 8 provides a list of genes up-related in cancer cells and a list of genes down-regulated in cancer cells.

DEFINITIONS

Figure 1:
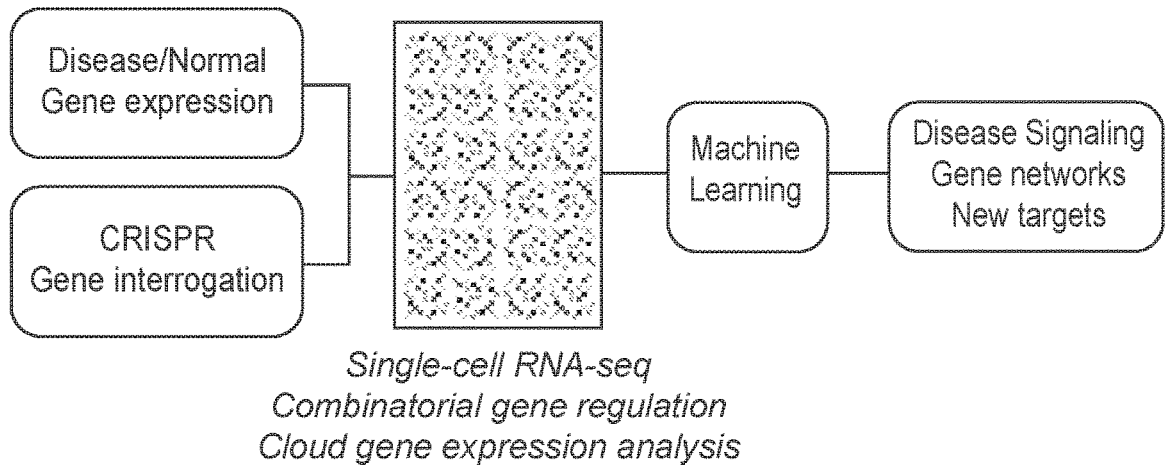
FIG. 1. An intelligent functional genomics platform for target identification and validation. CRISPR allows rapid gene interrogation, combined with single-cell RNAseq (scRNAseq) can further generate unique datasets of molecular features. With the data collected, disease signalling and gene networks can be dissected by machine learning algorithms, enabling new target identification and validation.

A "database" is an organized collection of data. Such databases are also, in some instances, referred to as knowledge bases. For instance, database may refer to a collection of data used to analyze and respond to queries. In certain embodiments, it includes one or more datasets, data groups, and/or metadata for organizing the datasets in a particular hierarchy or directory (e.g., a hierarchy of studies and projects). In addition, a database may include information correlating datasets to one another and to data groups, a list of globally unique terms or identifiers for genes or other features, such as lists of features measured on different platforms or in different experiments, total number of features in different organisms, their corresponding transcripts, protein products and their relationships.

A typical biological experiment determines expression or other information about a gene or other data associated with a particular cell type or tissue type. Other types of genetic features for which experimental information may be collected in raw data include SNP patterns (e.g., haplotype blocks), portions of genes (e.g., exons/introns or regulatory motifs), regions of a genome of chromosome spanning more than one gene, etc. Other types of biological features include phenotypic features such as the morphology of cells and cellular organelles such as nuclei, Golgi, etc.

The term "raw data", generally describes data from one or more experiments that provides information about one or more samples. Typically, raw data is not yet processed to a point suitable for use in the core components of the methods of the disclosure may be subject to pre-processing. Subsequent manipulation (e.g., pre-processing) reduces or manipulates raw data to a form suitable for use in a database and/or by one or more systems, e.g., systems employing an algorithm as described herein. The process of converting the raw data to feature sets is sometimes referred to as pre-processing.

As used herein "data import" is the process of bringing data into a database base or other repository in the system, and is an operation used in manipulating and/or analyzing and/or processing data. A user interface may facilitate data input by allowing the user to specify the experiment, its association with a particular study and/or project, and an experimental platform (e.g., an sequencing platform), and to identify key concepts with which to tag the data. In certain embodiments, data import also includes automated operations of decompressing, converting, copying, transferring, and/or tagging data, as well as, in some instances, mapping the imported data to data already in the system.

As should be apparent, certain embodiments of the invention employ processes acting under control of instructions and/or data stored in or transferred through one or more computer systems. Certain embodiments also relate to an apparatus for performing these operations. This apparatus may be specially designed and/or constructed for the required purposes, or it may be a general-purpose computer selectively configured by one or more computer programs and/or data structures stored in or otherwise made available to the computer. The processes presented herein are not inherently related to any particular computer or other apparatus. In particular, various general-purpose machines may be used with programs written in accordance with the teachings herein, or it may be more convenient to construct a more specialized apparatus to perform the required method steps. A particular structure for a variety of these machines is shown and described below.

Examples of displays suitable for interfacing with a user in accordance with the invention include but are not limited to cathode ray tube displays, liquid crystal displays, plasma displays, touch screen displays, video projection displays, light-emitting diode and organic light-emitting diode displays, surface-conduction electron-emitter displays and the like. Examples of printers include toner-based printers, liquid inkjet printers, solid ink printers, dye-sublimation printers as well as inkless printers such as thermal printers. Printing may be to a tangible medium such as paper or transparencies.

Examples of tangible computer-readable media suitable for use computer program products and computational apparatus of this invention include, but are not limited to, magnetic media such as hard disks, floppy disks, and magnetic tape; optical media such as CD-ROM disks; magneto-optical media; semiconductor memory devices (e.g., flash memory), and hardware devices that are specially configured to store and perform program instructions, such as read-only memory devices (ROM) and random access memory (RAM) and sometimes application-specific integrated circuits (ASICs), programmable logic devices (PLDs) and signal transmission media for delivering computer-readable instructions, such as local area networks, wide area networks, and the Internet. The data and program instructions provided herein may also be embodied on a carrier wave or other transport medium (including electronic or optically conductive pathways). The data and program instructions of this invention may also be embodied on a carrier wave or other transport medium (e.g., optical lines, electrical lines, and/or airwaves)

Examples of program instructions include low-level code, such as that produced by a compiler, as well as higher-level code that may be executed by the computer using an interpreter. Further, the program instructions may be machine code, source code and/or any other code that directly or indirectly controls operation of a computing machine. The code may specify input, output, calculations, conditionals, branches, iterative loops, etc.

User terminals may include any type of computer (e.g., desktop, laptop, tablet, etc.), media computing platforms (e.g., cable, satellite set top boxes, digital video recorders, etc.), handheld computing devices (e.g., PDAs, e-mail clients, etc.), cell phones or any other type of computing or communication platforms. A server system in communication with a user terminal may include a server device or decentralized server devices, and may include mainframe computers, mini computers, super computers, personal computers, or combinations thereof. A plurality of server systems may also be used without departing from the scope of the present invention. User terminals and a server system may communicate with each other through a network. The network may comprise, e.g., wired networks such as LANs (local area networks), WANs (wide area networks), MANs (metropolitan area networks), ISDNs (Integrated Service Digital Networks), etc. as well as wireless networks such as wireless LANs, CDMA, Bluetooth, and satellite communication networks, etc. without limiting the scope of the present invention.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (e.g., DNA exogenous to the cell) into the cell. Genetic change ("modification") can be accomplished either by incorporation of the new nucleic acid into the genome of the host cell, or by transient or stable maintenance of the new nucleic acid as an episomal element. Where the cell is a eukaryotic cell, a permanent genetic change is generally achieved by introduction of new DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al., Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a genetically modified eukaryotic host cell is a genetically modified eukaryotic host cell that contains, by virtue of introduction into a suitable eukaryotic host cell of a heterologous nucleic acid, an exogenous nucleic acid that is foreign to the eukaryotic host cell, or a recombinant nucleic acid that is not normally found in the eukaryotic host cell.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a CRISPR/Cas effector polypeptide" includes a plurality of such CRISPR/Cas effector polypeptides and reference to "the cancer-related phenotype" includes reference to one or more cancer-related phenotypes and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a method for identifying cancer treatment targets (or combinatorial cancer treatment targets). In some cases, the method comprises the steps of: (a) generating normal and cancer cells harboring a CRISPR/Cas effector polypeptide; (b) inhibiting expression of a target gene in the normal and cancer cells generated in step (a) by stably introducing an sgRNA expression construct directed to the target gene, thereby inhibiting expression of the target gene; (c) monitoring one or more molecular features and/or phenotypes (e.g., disease phenotypes) in the cells (e.g., by single-cell RNAseq (scRNAseq)) following inhibition of target gene expression; and (d) designating the molecular feature and disease phenotype as a target gene knockdown-related features and phenotypes (e.g., by use of an algorithm stored on a computer), if improvement in the molecular feature or phenotype is observed following step (b). In some cases, identification of treatment targets comprises combinatorial interrogations of multiple genes. In some cases, a method for identifying a cancer treatment target, the method comprises: (a) introducing a CRISPR/Cas effector polypeptide into a cancer cell and into a corresponding normal cell of the same cell type as the cancer cell; (b) introducing a CRISPR/Cas guide RNA targeting a gene of interest into the normal and cancer cells generated in step (a), thereby reducing expression of the target gene; (c) monitoring one or more molecular features and/or phenotypes in the cells following reduction of target gene expression; and (d) where the one or more molecular feature and disease phenotype indicates a reduction in the cancerous state of the cancer cell, identifying the target gene as a candidate cancer treatment target. In some cases, a method for identifying a cancer treatment target, or combinatorial cancer treatment targets, comprises: a) introducing into a cancer cell and into a corresponding normal cell of the same cell type as the cancer cell a CRISPR/Cas system comprising: i) a CRISPR/Cas effector polypeptide; and ii) one or more CRISPR/Cas guide RNAs, wherein said introducing reduces expression of a target gene targeted by the guide RNA (e.g., a target gene to which the guide RNA hybridizes); and b) assessing the effect of the reduced expression of the target gene on one or more molecular features and/or phenotypes in the cells. Where assessment of the one or more molecular features and/or phenotypes in the cells indicates that reduced expression of the target gene reduces the cancer phenotype of the cancer cell, the target gene is identified as a candidate target gene for cancer treatment. In some cases, the treatment targets comprise the combinatorial interrogations of multiple genes.

The present disclosure provides a method for identifying biomarkers and molecular features of normal and cancer cells. The method comprises the steps of: (a) single-cell RNAseq (scRNAseq) analysis of normal and cancer cells; (b) analyzing the single-cell RNAseq on a cloud platform; (c) classifying different types of cells; (d) developing computer algorithms; and (e) identifying biomarkers and molecular features of normal and cancer cells. In some cases, the biomarkers and molecular features comprises the combinatorial expressions of multiple genes.

Methods for Identifying Cancer Treatment Targets; Methods of Identifying Biomarkers of Normal and Cancer Cells The present disclosure provides a method for identifying cancer treatment targets. In some cases, the method comprises the steps of: (a) generating normal and cancer cells harboring a CRISPR/Cas effector polypeptide; (b) inhibiting expression of a target gene in the normal and cancer cells generated in step (a) by stably introducing an sgRNA expression construct directed to the target gene, thereby inhibiting expression of the target gene; (c) monitoring one or more molecular features and/or phenotypes (e.g., disease phenotypes) in the cells following inhibition of target gene expression; and (d) designating the molecular feature and disease phenotype as a target gene knockdown-related features and phenotypes, if improvement in the molecular feature or phenotype is observed following step (b). In some cases, a method for identifying a cancer treatment target, the method comprises: (a) introducing a CRISPR/Cas effector polypeptide into a cancer cell and into a corresponding normal cell of the same cell type as the cancer cell; (b) introducing a CRISPR/Cas guide RNA targeting a gene of interest into the normal and cancer cells generated in step (a), thereby reducing expression of the target gene; (c) monitoring one or more molecular features and/or phenotypes in the cells following reduction of target gene expression; and (d) where the one or more molecular feature and disease phenotype indicates a reduction in the cancerous state of the cancer cell, identifying the target gene as a candidate cancer treatment target. In some cases, a method for identifying a cancer treatment target, the method comprises: a) introducing into a cancer cell and into a corresponding normal cell of the same cell type as the cancer cell a CRISPR/Cas system comprising: i) a CRISPR/Cas effector polypeptide; and ii) one or more CRISPR/Cas guide RNAs, wherein said introducing reduces expression of a target gene targeted by the guide RNA (e.g., a target gene to which the guide RNA hybridizes); and b) assessing the effect of the reduced expression of the target gene on one or more molecular features and/or phenotypes in the cells. Where assessment of the one or more molecular features and/or phenotypes in the cells indicates that reduced expression of the target gene reduces the cancer phenotype of the cancer cell, the target gene is identified as a candidate target gene for cancer treatment.

The present disclosure also provides a method for identifying biomarkers and molecular features of normal and cancer cells. The method comprises the steps of: (a) single-cell RNAseq (scRNAseq) analysis of normal and cancer cells; (b) analyzing the single-cell RNAseq on a cloud platform; (c) classifying different types of cells; (d) developing computer algorithms; and (e) identifying biomarkers and molecular features of normal and cancer cells. In some cases, the biomarkers and molecular features comprise combinatorial expressions of multiple genes.

Reduced expression of a target gene can result in reduction in cancerous characteristics of the cancer cell. For example, reduced expression of a target gene can result in a reduction in cancer phenotype; e.g., where the cancer phenotype is a morphological feature characteristic of the cancer cell. As another example, reduced expression of a target gene can result in a reduction of one or more biomarkers characteristic of the cancer cell. Reduced expression of a target gene can result in the cancer cell appearing more like the corresponding normal cell, e.g., in morphological appearance, in gene expression profile, in biomarker expression, and the like.

As noted above, a method of the present disclosure comprises introducing into normal and cancer cells a CRISPR/Cas system (i.e., a CRISPR/Cas effector polypeptide and one or more guide RNAs). The normal and cancer cells are generally of the same cell type. For example, in some cases, a method of the present disclosure comprises: i) introducing a CRISPR/Cas system into a normal (non-cancerous) cell; and ii) introducing the same CRISPR/Cas system into a cancerous cell of the same cell type as the normal cell. In some cases, the cells are primary cells. In some cases, a method of the present disclosure comprises: i) introducing a CRISPR/Cas system into a normal (non-cancerous) pancreatic cell; and ii) introducing the same CRISPR/Cas system into a pancreatic cancer cell. In some cases, a method of the present disclosure comprises: i) introducing a CRISPR/Cas system into a normal (non-cancerous) pancreatic acinar cell; and ii) introducing the same CRISPR/Cas system into a cancerous pancreatic acinar cell. In some cases, a method of the present disclosure comprises: i) introducing a CRISPR/Cas system into a normal (non-cancerous) pancreatic ductal cell; and ii) introducing the same CRISPR/Cas system into a cancerous pancreatic ductal cell. In some cases, a method of the present disclosure comprises: i) introducing a CRISPR/Cas system into a normal (non-cancerous) brain cell; and ii) introducing the same CRISPR/Cas system into a brain cancer cell (e.g., a glioblastoma, a neuroblastoma, and the like). In some cases, a method of the present disclosure comprises: i) introducing a CRISPR/Cas system into a normal (non-cancerous) liver cell; and ii) introducing the same CRISPR/Cas system into a liver cancer cell. In some cases, a method of the present disclosure comprises: i) introducing a CRISPR/Cas system into a normal (non-cancerous) kidney cell; and ii) introducing the same CRISPR/Cas system into a kidney cancer cell (e.g., a nephroma, etc.). In some cases, a method of the present disclosure comprises: i) introducing a CRISPR/Cas system into a normal (non-cancerous) ovarian cell; and ii) introducing the same CRISPR/Cas system into an ovarian cancer cell. In some cases, a method of the present disclosure comprises: i) introducing a CRISPR/Cas system into a normal (non-cancerous) breast cell; and ii) introducing the same CRISPR/Cas system into a breast cancer cell. In some cases, a method of the present disclosure comprises: i) introducing a CRISPR/Cas system into a normal (non-cancerous) colon cell; and ii) introducing the same CRISPR/Cas system into a colon cancer cell. In some cases, a method of the present disclosure comprises: i) introducing a CRISPR/Cas system into a normal (non-cancerous) bone cell; and ii) introducing the same CRISPR/Cas system into a bone cancer cell. In some cases, a method of the present disclosure comprises: i) introducing a CRISPR/Cas system into a normal (non-cancerous) immune cell (e.g., T cell; B cell; myeloid cell; etc.); and ii) introducing the same CRISPR/Cas system into a cancerous immune cell. In some cases, a method of the present disclosure comprises: i) introducing a CRISPR/Cas system into a normal (non-cancerous) skin cell; and ii) introducing the same CRISPR/Cas system into a cancerous skin cell (e.g., a melanoma).

The cancer cell can be, e.g., any one of the following: adenocarcinoma, adrenal gland cortical carcinoma, adrenal gland neuroblastoma, anus squamous cell carcinoma, appendix adenocarcinoma, bladder urothelial carcinoma, bile duct adenocarcinoma, bladder carcinoma, bladder urothelial carcinoma, bone chordoma, bone marrow leukemia lymphocytic chronic, bone marrow leukemia non-lymphocytic acute myelocytic, bone marrow lymph proliferative disease, bone marrow multiple myeloma, bone sarcoma, brain astrocytoma, brain glioblastoma, brain medulloblastoma, brain meningioma, brain oligodendroglioma, breast adenoid cystic carcinoma, breast carcinoma, breast ductal carcinoma in situ, breast invasive ductal carcinoma, breast invasive lobular carcinoma, breast metaplastic carcinoma, cervix neuroendocrine carcinoma, cervix squamous cell carcinoma, colon adenocarcinoma, colon carcinoid tumor, duodenum adenocarcinoma, endometrioid tumor, esophagus adenocarcinoma, esophagus and stomach carcinoma, eye intraocular melanoma, eye intraocular squamous cell carcinoma, eye lacrimal duct carcinoma, fallopian tube serous carcinoma, gallbladder adenocarcinoma, gallbladder *glomus* tumor, gastroesophageal junction adenocarcinoma, head and neck adenoid cystic carcinoma, head and neck carcinoma, head and neck neuroblastoma, head and neck squamous cell carcinoma, kidney chromophore carcinoma, kidney medullary carcinoma, kidney renal cell carcinoma, kidney renal papillary carcinoma, kidney sarcomatoid carcinoma, kidney urothelial carcinoma, kidney carcinoma, leukemia lymphocytic, leukemia lymphocytic chronic, liver cholangiocarcinoma, liver hepatocellular carcinoma, liver carcinoma, lung adenocarcinoma, lung adenosquamous carcinoma, lung atypical carcinoid, lung carcinosarcoma, lung large cell neuroendocrine carcinoma, lung non-small cell lung carcinoma, lung sarcoma, lung sarcomatoid carcinoma, lung small cell carcinoma, lung small cell undifferentiated carcinoma, lung squamous cell carcinoma, upper aerodigestive tract squamous cell carcinoma, upper aerodigestive tract carcinoma, lymph node lymphoma diffuse large B cell, lymph node lymphoma follicular lymphoma, lymph node lymphoma mediastinal B-cell, lymph node lymphoma plasmablastic lung adenocarcinoma, lymphoma follicular lymphoma, lymphoma, non-Hodgkins lymphoma, nasopharynx and paranasal sinuses undifferentiated carcinoma, ovary carcinoma, ovary carcinosarcoma, ovary clear cell carcinoma, ovary epithelial carcinoma, ovary granulosa cell tumor, ovary serous carcinoma, pancreas carcinoma, pancreas ductal adenocarcinoma, pancreas neuroendocrine carcinoma, peritoneum mesothelioma, peritoneum serous carcinoma, placenta choriocarcinoma, pleura mesothelioma, prostate acinar adenocarcinoma, prostate carcinoma, rectum adenocarcinoma, rectum squamous cell carcinoma, skin adnexal carcinoma, skin basal cell carcinoma, skin melanoma, skin Merkel cell carcinoma, skin squamous cell carcinoma, small intestine adenocarcinoma, small intestine gastrointestinal stromal tumors (GISTs), large intestine/colon carcinoma, large intestine adenocarcinoma, soft tissue angiosarcoma, soft tissue Ewing sarcoma, soft tissue hemangioendothelioma, soft tissue inflammatory myofibroblastic tumor, soft tissue leiomyosarcoma, soft tissue liposarcoma, soft tissue neuroblastoma, soft tissue paraganglioma, soft tissue perivascular epithelioid cell tumor, soft tissue sarcoma, soft tissue synovial sarcoma, stomach adenocarcinoma, stomach adenocarcinoma diffuse-type, stomach adenocarcinoma intestinal type, stomach adenocarcinoma intestinal type, stomach leiomyosarcoma, thymus carcinoma, thymus thymoma lymphocytic, thyroid papillary carcinoma, unknown primary adenocarcinoma, unknown primary carcinoma, unknown primary malignant neoplasm, lymphoid neoplasm, unknown primary melanoma, unknown primary sarcomatoid carcinoma, unknown primary squamous cell carcinoma, unknown undifferentiated neuroendocrine carcinoma, unknown primary undifferentiated small cell carcinoma, uterus carcinosarcoma, uterus endometrial adenocarcinoma, uterus endometrial adenocarcinoma endometrioid, uterus endometrial adenocarcinoma papillary serous, and uterus leiomyosarcoma. The non-cancerous ("normal") cell can be a cell of the same cell type as the cancerous cell. The cancer cell can be, e.g., any one of the following: an acute myeloid leukemia (AML), breast carcinoma, cholangiocarcinoma, colorectal adenocarcinoma, extrahepatic bile duct adenocarcinoma, female genital tract malignancy, gastric adenocarcinoma, gastroesophageal adenocarcinoma, gastrointestinal stromal tumor (GIST), glioblastoma, head and neck squamous carcinoma, leukemia, liver hepatocellular carcinoma, low grade glioma, lung bronchioloalveolar carcinoma (BAC), non-small cell lung cancer (NSCLC), small cell lung cancer (SCLC), lymphoma, male genital tract malignancy, malignant solitary fibrous tumor of the pleura (MSFT), melanoma, multiple myeloma, neuroendocrine tumor, nodal diffuse large B-cell lymphoma, non epithelial ovarian cancer (non-EOC), ovarian surface epithelial carcinoma, pancreatic adenocarcinoma, pituitary carcinomas, oligodendroglioma, prostatic adenocarcinoma, retroperitoneal or peritoneal carcinoma, retroperitoneal or peritoneal sarcoma, small intestinal malignancy, soft tissue tumor, thymic carcinoma, thyroid carcinoma, or uveal melanoma. The cancer may be an acute lymphoblastic leukemia; acute myeloid leukemia; adrenocortical carcinoma; AIDS-related cancer; AIDS-related lymphoma; anal cancer; appendix cancer; astrocytomas; atypical teratoid/rhabdoid tumor; basal cell carcinoma; bladder cancer; brain stem glioma; brain tumor, brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma; breast cancer; bronchial tumors; Burkitt lymphoma; cancer of unknown primary site (CUP); carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; or Wilm's tumor. The non-cancerous ("normal") cell can be a cell of the same cell type as the cancerous cell.

A guide RNA that is introduced into both a cancerous cell and a non-cancerous cell of the same cell type as the cancerous cell can be selected based on predetermined criteria, or can be random. For example, a guide RNA that is introduced into both a cancerous cell and a non-cancerous cell of the same cell type as the cancerous cell can be one that is targeted to a gene that is suspected of being involved in tumorigenesis. As another example, a guide RNA that is introduced into both a cancerous cell and a non-cancerous cell of the same cell type as the cancerous cell can be one that is targeted to a gene that is suspected of being involved in cell cycle control. For example, guide RNAs can be targeted to genes up-regulated in cancer cells. As another example, guide RNAs can be targeted to genes down-regulated in cancer cells. FIG. 8 provides an example of genes up-regulated or down-regulated in cancer cells; guide RNAs targeting these sets of target genes can be introduced into, e.g., ductal and acinar cells and corresponding normal ductal and acinar cells.

In some cases, a library of sgRNAs is introduced into a plurality of cancer cells and a plurality of corresponding normal cells (non-cancerous cells of the same cell type as the cancer cells), such that, on average, one species of sgRNA is introduced into one cell. A sgRNA library can have from 10 to $10^6$ different members (member sgRNAs that differ from one another in nucleotide sequence and that target different target genes). A sgRNA library can have from 10 to $10^2$ member sgRNAs, from $10^2$ to $10^3$ member sgRNAs, from $10^3$ to $10^4$ member sgRNAs, from $10^4$ to $10^5$ member sgRNAs, or from $10^5$ to $10^6$ member sgRNAs. A sgRNA library can have more than $10^6$ member sgRNAs.

For example, where the cancerous and non-cancerous cells are pancreatic cells, the guide RNA can be targeted to one or more of the target genes listed in FIG. 4A (and FIG. 8).

To determine the effect of inhibiting or activating a target gene in a cancer cell, compared to the non-cancerous normal cell, molecular features and/or phenotypes can be assessed. For example, in some cases, expression levels of particular genes are assessed to determine the effect of inhibiting or activating a target gene in a cancer cell, compared to the non-cancerous normal cell. For example, to determine the effect of inhibiting or activating a target gene in a cancer cell, gene expression levels of one or more of a variety of indicator genes can be assessed. Suitable indicator genes include, e.g., cell cycle control genes, oncogenes, transcription factors, and the like. Suitable genes include those depicted in FIG. 3, e.g., Abat, Acpp, Amt, Avpr1b, Bcl2, Ccbl1, Ccnd1, Dhps, Fgf1, Impdh1, Kif11, Ldlr, Nos1, Pdgfrb, Rarg, Th, Txnrd1, Ube1x, Dtymk, Frap1, Pola1, Hsp90ab1, Btk, Src, Clcnkb, Rac1, Top2a, Mmp16, Vdac2, Ikbkb, Lig3, Parp1, Hck, and Cdk9. Expression levels can be determined using any of a variety of methods, many of which are known in the art. Such methods include, e.g., single-cell RNA sequencing; polymerase chain reaction (PCR); and the like.

In some cases, the effect of inhibiting or activating a target gene in a cancer cell, compared to the non-cancerous normal cell comprises assessing a biomarker in the cancer cell and the corresponding non-cancer cell. The biomarker can be any useful biological molecule or entity, including without limitation a protein (including a polypeptide or peptide), nucleic acid, lipid, carbohydrate, or a combination of any combination thereof. Nucleic acids include without limitation deoxyribonucleic acid (DNA) and ribonucleic acids (RNA), such as messenger RNA (mRNA), transfer RNA (tRNA), small RNAs, non-coding RNAs, and microRNAs. Any useful characteristic can be determined for a marker/biomarker, including without limitation a concentration, expression level, copy number, amino acid or nucleic acid sequence. Sequences can be assessed for various characteristics, including without limitation at least one of a mutation, a polymorphism, a deletion, an insertion, a substitution, a translocation, a fusion, a break, a duplication, an amplification, a repeat, a copy number variant (CNV), a DNA methylation variation, a transcript expression level, a transcript variant, and a splice variant.

A biomarker status can be determined by any appropriate laboratory technique for assessing a molecule in a biological sample. The technique may comprise gene expression analysis, nucleic acid sequence analysis, nucleic acid methylation analysis and/or proteomic analysis. Techniques for assessing such markers include but are not limited to, nucleic acid sequencing, such as a DNA sequencing or RNA sequencing; protein immunoassays such as Western blots, ELISA or immunohistochemistry (IHC); nucleic acid analysis such in situ hybridization (ISH), including fluorescent in situ hybridization (FISH) and/or chromogenic in situ hybridization (CISH); nucleic acid amplification (e.g., polymerase chain reaction (PCR), and quantitative varieties thereof including qPCR or RT-PCR); various types of microarray (mRNA expression arrays, PCR-based low density arrays, protein arrays, etc.); various types of nucleic acid sequencing (Sanger, pyrosequencing, etc.); comparative genomic hybridization (CGH); high throughput sequencing (HTS) or Next Generation sequencing (NGS) of nucleic acids; Northern blot for RNA; Southern blot for DNA; flow cytometry; nucleic acid methylation analysis; nucleic acid fragment analysis; gel electrophoresis; and any other appropriate technique to assay the presence or quantity of a biological molecule of interest. In some cases, the biomarker comprises one or more of: 1p19q, ABL1, AKT1, ALK, APC, AR, ATM, BRAF, BRCA1, BRCA2, cKIT, cMET, CSF1R, CTNNB1, EGFR, EGFRvIII, ER, ERBB2 (HER2), ERCC1, FGFR1, FGFR2, FLT3, GNA11, GNAQ, GNAS, H3K36me3, HER2, HRAS, IDH1, IDH2, JAK2, KDR (VEGFR2), KRAS, MDM2, MGMT, MLH1, MPL, NOTCH1, NRAS, PBRM1, PD1, PDL1, PDGFRA, Pgp, PIK3CA, PR, PTEN, RET, RRM1, SMO, SPARC, TLE3, TOP2A, TOPO1, TP53, TS, TUBB3, VHL, MLH1, MSH2, MSH6, PMS2, microsatellite instability (MSI) and ROS1. The biomarker may also include at least one of CAIX, hENT1, IDO, LAG3, RET, and NTRK1 (NTRK, TRK).

In some cases, the effect of inhibiting or activating a target gene in a cancer cell, compared to the non-cancerous normal cell comprises histological analysis of the cancer cell and the corresponding non-cancerous cell. For example, morphological changes can be assessed.

In some cases, a CRISPR/Cas system that is introduced into both a cancerous cell and a non-cancerous cell of the same cell type as the cancerous cell comprises: a) a CRISPR/Cas fusion polypeptide comprising: i) an enzymatically inactive CRISPR/Cas effector polypeptide that retains target nucleic acid binding; and ii) a transcriptional repressor polypeptide. In these instances, the CRISPR/Cas system reduces expression of a target gene. Where reduction of target gene expression reduces one or more molecular features and/or phenotypes associated with the cancer cell compared to the non-cancer cell, the target gene is considered a target for cancer treatment.

In some cases, CRISPR/Cas system that is introduced into both a cancerous cell and a non-cancerous cell of the same cell type as the cancerous cell comprises: a) a CRISPR/Cas fusion polypeptide comprising: i) an enzymatically inactive CRISPR/Cas effector polypeptide that retains target nucleic acid binding; and ii) a transcriptional activator polypeptide. In these instances, the CRISPR/Cas system increases expression of a target gene. Where an increase of target gene expression reduces one or more molecular features and/or phenotypes associated with the cancer cell compared to the non-cancer cell, the target gene is considered a target for cancer treatment.

In some cases, CRISPR/Cas system that is introduced into both a cancerous cell and a non-cancerous cell of the same cell type as the cancerous cell comprises: i) an enzymatically active CRISPR/Cas effector polypeptide; and ii) two guide RNAs, where the CRISPR/Cas system results in deletion of all or a portion of a target gene. In these instances, the CRISPR/Cas system reduces expression of the target gene. Where reduction of target gene expression reduces one or more molecular features and/or phenotypes associated with the cancer cell compared to the non-cancer cell, the target gene is considered a target for cancer treatment.

CRISPR/Cas Effector Systems

Any of a variety of CRISPR/Cas systems can be used in a method of the present disclosure. A CRISPR/Cas system comprises: a) a CRISPR/Cas effector polypeptide; and b) a guide RNA (e.g., a single-molecule guide RNA or a dual-molecule guide RNA). CRISPR/Cas system suitable for use in a method of the present disclosure can comprise: i) an enzymatically active CRISPR/Cas effector polypeptide; ii) a CRISPRi effector polypeptide (e.g., CRISPR interference, a catalytically dead Cas9 fused to a transcriptional repressor peptide, such as KRAB); or iii) a CRISPRa effector polypeptide (CRISPR activation, a catalytically inactive CRISPR/Cas effector polypeptide fused to a transcriptional activator peptide, such as VPR).

CRISPR/Cas Effector Polypeptides

In class 2 CRISPR systems, the functions of the effector complex (e.g., the cleavage of target DNA) are carried out by a single endonuclease (e.g., see Zetsche et al., Cell. 2015 Oct. 22; 163(3):759-71; Makarova et al., Nat Rev Microbiol. 2015 Nov. 13(11):722-36; Shmakov et al., Mol Cell. 2015 Nov. 5; 60(3):385-97); and Shmakov et al. (2017) *Nature Reviews Microbiology* 15:169. As such, the term "class 2 CRISPR/Cas protein" is used herein to encompass the CRISPR/Cas effector polypeptide (e.g., the target nucleic acid binding protein or the target nucleic acid binding and cleaving protein) from class 2 CRISPR systems. Thus, the term "class 2 CRISPR/Cas effector polypeptide" as used herein encompasses type II CRISPR/Cas effector polypeptides (e.g., Cas9); type V-A CRISPR/Cas effector polypeptides (e.g., Cpf1 (also referred to a "Cas12a")); type V-B CRISPR/Cas effector polypeptides (e.g., C2c1 (also referred to as "Cas12b")); type V-C CRISPR/Cas effector polypeptides (e.g., C2c3 (also referred to as "Casl2c")); type V-U1 CRISPR/Cas effector polypeptides (e.g., C2c4); type V-U2 CRISPR/Cas effector polypeptides (e.g., C2c8); type V-U5 CRISPR/Cas effector polypeptides (e.g., C2c5); type V-U4 CRISPR/Cas proteins (e.g., C2c9); type V-U3 CRISPR/Cas effector polypeptides (e.g., C2c10); type VI-A CRISPR/Cas effector polypeptides (e.g., C2c2 (also known as "Casl3a")); type VI-B CRISPR/Cas effector polypeptides (e.g., Cas13b (also known as C2c4)); and type VI-C CRISPR/Cas effector polypeptides (e.g., Casl3c (also known as C2c7)). To date, class 2 CRISPR/Cas effector polypeptides encompass type II, type V, and type VI CRISPR/Cas effector polypeptides, but the term is also meant to encompass any class 2 CRISPR/Cas effector polypeptide suitable for binding to a corresponding guide RNA and forming an RNP complex.

Type II CRISPR/Cas Endonucleases (e.g., Cas 9)

In natural Type II CRISPR/Cas systems, Cas9 functions as an RNA-guided endonuclease that uses a dual-guide RNA having a crRNA and trans-activating crRNA (tracrRNA) for target recognition and cleavage by a mechanism involving two nuclease active sites in Cas9 that together generate double-stranded DNA breaks (DSBs), or can individually generate single-stranded DNA breaks (SSBs). The Type II CRISPR endonuclease Cas9 and engineered dual-(dgRNA) or single guide RNA (sgRNA) form a ribonucleoprotein (RNP) complex that can be targeted to a desired DNA sequence. Guided by a dual-RNA complex or a chimeric single-guide RNA, Cas9 generates site-specific DSBs or SSBs within double-stranded DNA (dsDNA) target nucleic acids, which are repaired either by non-homologous end joining (NHEJ) or homology-directed recombination (HDR).

A type II CRISPR/Cas effector polypeptide is a type of class 2 CRISPR/Cas endonuclease. In some cases, the type II CRISPR/Cas endonuclease is a Cas9 protein. A Cas9 protein forms a complex with a Cas9 guide RNA. The guide RNA provides target specificity to a Cas9-guide RNA complex by having a nucleotide sequence (a guide sequence) that is complementary to a sequence (the target site) of a target nucleic acid (as described elsewhere herein). The Cas9 protein of the complex provides the site-specific activity. In other words, the Cas9 protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA.

A Cas9 protein can bind and/or modify (e.g., cleave, nick, methylate, demethylate, etc.) a target nucleic acid and/or a polypeptide associated with target nucleic acid (e.g., methylation or acetylation of a histone tail)(e.g., when the Cas9 protein includes a fusion partner with an activity). In some cases, the Cas9 protein is a naturally-occurring protein (e.g., naturally occurs in bacterial and/or archaeal cells). In other cases, the Cas9 protein is not a naturally-occurring polypeptide (e.g., the Cas9 protein is a variant Cas9 protein, a chimeric protein, and the like). Examples of suitable Cas9 proteins include, but are not limited to, those set forth in SEQ ID NOs: 5-816. Naturally occurring Cas9 proteins bind a Cas9 guide RNA, are thereby directed to a specific sequence within a target nucleic acid (a target site), and cleave the target nucleic acid (e.g., cleave dsDNA to generate a double strand break, cleave ssDNA, cleave ssRNA, etc.). A chimeric Cas9 protein is a fusion protein comprising a Cas9 polypeptide that is fused to a heterologous protein (referred to as a fusion partner), where the heterologous protein provides an activity (e.g., one that is not provided by the Cas9 protein). The fusion partner can provide an activity, e.g., enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases, a portion of the Cas9 protein (e.g., the RuvC domain and/or the HNH domain) exhibits reduced nuclease activity relative to the corresponding portion of a wild type Cas9 protein (e.g., in some cases the Cas9 protein is a nickase). In some cases, the Cas9 protein is enzymatically inactive, or has reduced enzymatic activity relative to a wild-type Cas9 protein (e.g., relative to *Streptococcus pyogenes* Cas9).

In some cases, a fusion protein comprises: a) a catalytically inactive Cas9 protein (or other catalytically inactive CRISPR effector polypeptide); and b) a catalytically active endonuclease. For example, in some cases, the catalytically active endonuclease is a FokI polypeptide. As one non-limiting example, in some cases, a fusion protein comprises: a) a catalytically inactive Cas9 protein (or other catalytically inactive CRISPR effector polypeptide); and b) is a FokI nuclease comprising an amino acid sequence having at least at least 85%, at least 90%, at least 95%, at id least 98%, at least 99%, or 100%, amino acid sequence identity to the FokI amino acid sequence provided below; where the FokI nuclease has a length of from about 195 amino acids to about 200 amino acids.

FokI Nuclease Amino Acid Sequence:

(SEQ ID NO: 817)
QLVKSELEEKKSELRHKLKYVPHEYIELIEIARNSTQDRILEMKVMEFFM

KVYGYRGKHLGGSRKPDGAIYTVGSPIDYGVIVDTKAYSGGYNLPIGQAD

EMQRYVEENQTRNKHINPNEWWKVYPSSVTEFKFLFVSGHFKGNYKAQLT

RLNHITNCNGAVLSVEELLIGGEMIKAGTLTLEEVRRKFNNGEINF.

Assays to determine whether given protein interacts with a Cas9 guide RNA can be any convenient binding assay that tests for binding between a protein and a nucleic acid. Suitable binding assays (e.g., gel shift assays) will be known to one of ordinary skill in the art (e.g., assays that include adding a Cas9 guide RNA and a protein to a target nucleic acid).

Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art and can include adding a Cas9 guide RNA and a protein to a target nucleic acid.

Many Cas9 orthologs from a wide variety of species have been identified and in some cases the proteins share only a few identical amino acids. Identified Cas9 orthologs have similar domain architecture with a central HNH endonuclease domain and a split RuvC/RNaseH domain (e.g., RuvCI, RuvCII, and RuvCIII) (e.g., see Table 1). For example, a Cas9 protein can have 3 different regions (sometimes referred to as RuvC-I, RuvC-II, and RucC-III), that are not contiguous with respect to the primary amino acid sequence of the Cas9 protein, but fold together to form a RuvC domain once the protein is produced and folds. Thus, Cas9 proteins can be said to share at least 4 key motifs with a conserved architecture. Motifs 1, 2, and 4 are RuvC like motifs while motif 3 is an HNH-motif. The motifs set forth in Table 1 may not represent the entire RuvC-like and/or HNH domains as accepted in the art, but Table 1 does present motifs that can be used to help determine whether a given protein is a Cas9 protein.

TABLE 1

Table 1 lists 4 motifs that are present in Cas9 sequences from various species. The amino acids listed in Table 1 are from the Cas9 from *S. pyogenes* (SEQ ID NO: 5).

| Motif # | Motif | Amino acids (residue #s) | Highly conserved |
|---|---|---|---|
| 1 | RuvC-like I | IGLDIGTNSVGWAVI (7-21) (SEQ ID NO: 1) | D10, G12, G17 |
| 2 | RuvC-like II | IVIEMARE (759-766) (SEQ ID NO: 2) | E762 |
| 3 | HNH-motif | DVDHIVPQSFLKDDSIDNKVLTRSDK N (837-863)(SEQ ID NO: 3) | H840, N854, N863 |
| 4 | RuvC-like III | HHAHDAYL (982-989) (SEQ ID NO: 4) | H982, H983, A984, D986, A987 |

In some cases, a suitable Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 as set forth in SEQ ID NOs: 1-4, respectively (e.g., see Table 1), or to the corresponding portions in any of the amino acid sequences set forth in SEQ ID NOs: 5-816.

In other words, in some cases, a suitable Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816.

In some cases, a suitable Cas9 protein comprises an amino acid sequence having 4 motifs, each of motifs 1-4 having 60% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 70% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 75% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 80% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 85% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 90% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 95% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 99% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 100% amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable Cas9 protein comprises an amino acid sequence having 60% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 70% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 75% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 80% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 85% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 90% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 95% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 99% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to the Cas9 amino acid sequence set forth in SEQ ID NO: 5, or to any of the amino acid sequences set forth as SEQ ID NOs: 6-816.

In some cases, a suitable Cas9 protein comprises an amino acid sequence having 60% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 70% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 75% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 80% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 85% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 90% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 95% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 99% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 100% amino acid sequence identity to the Cas9 amino acid sequence set forth in SEQ ID NO: 5, or to any of the amino acid sequences set forth as SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a Cas9 protein comprises 4 motifs (as listed in Table 1), at least one with (or each with) amino acid sequences having 75% or more, 80% or more, 85% or more, 90% or more, 95% or more, 99% or more or 100% amino acid sequence identity to each of the 4 motifs listed in Table 1 (SEQ ID NOs:1-4), or to the corresponding portions in any of the amino acid sequences set forth as SEQ ID NOs: 6-816.

Examples of various Cas9 proteins (and Cas9 domain structure) and Cas9 guide RNAs (as well as information regarding requirements related to protospacer adjacent motif (PAM) sequences present in targeted nucleic acids) can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 Sep. 31(9):839-43; Qi et al., Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 Oct. 23(10):1163-71; Cho et al., Genetics. 2013 November; 195 (3):1177-80; DiCarlo et al., Nucleic Acids Res. 2013 April; 41(7):4336-43; Dickinson et al., Nat Methods. 2013 Oct. 10(10):1028-34; Ebina et al., Sci Rep. 2013; 3:2510; Fujii et al., Nucleic Acids Res. 2013 Nov. 1; 41(20):e187; Hu et al., Cell Res. 2013 Nov. 23(11):1322-5; Jiang et al., Nucleic Acids Res. 2013 Nov. 1; 41(20):e188; Larson et al., Nat Protoc. 2013 Nov. 8(11):2180-96; Mali et al., Nat Methods. 2013 Oct. 10(10):957-63; Nakayama et al., Genesis. 2013 December; 51(12):835-43; Ran et al., Nat Protoc. 2013 Nov. 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; Shmakov et al., Nat Rev Microbiol. 2017 Mar. 15(3):169-182; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

Variant Cas9 Proteins—Nickases and dCas9

In some cases, a Cas9 protein is a variant Cas9 protein. A variant Cas9 protein has an amino acid sequence that is different by at least one amino acid (e.g., has a deletion, insertion, substitution, fusion) when compared to the amino acid sequence of a corresponding wild type Cas9 protein. In some instances, the variant Cas9 protein has an amino acid change (e.g., deletion, insertion, or substitution) that reduces the nuclease activity of the Cas9 protein. For example, in some instances, the variant Cas9 protein has 50% or less, 40% or less, 30% or less, 20% or less, 10% or less, 5% or less, or 1% or less of the nuclease activity of the corresponding wild-type Cas9 protein. In some cases, the variant Cas9 protein has no substantial nuclease activity. When a Cas9 protein is a variant Cas9 protein that has no substantial nuclease activity, it can be referred to as a nuclease defective Cas9 protein or "dCas9" for "dead" Cas9. A protein (e.g., a class 2 CRISPR/Cas protein, e.g., a Cas9 protein) that cleaves one strand but not the other of a double stranded target nucleic acid is referred to herein as a "nickase" (e.g., a "nickase Cas9").

In some cases, a variant Cas9 protein can cleave the complementary strand (sometimes referred to in the art as the target strand) of a target nucleic acid but has reduced ability to cleave the non-complementary strand (sometimes referred to in the art as the non-target strand) of a target nucleic acid. For example, the variant Cas9 protein can have a mutation (amino acid substitution) that reduces the function of the RuvC domain. Thus, the Cas9 protein can be a nickase that cleaves the complementary strand, but does not cleave the non-complementary strand. As a non-limiting example, in some embodiments, a variant Cas9 protein has a mutation at an amino acid position corresponding to residue D10 (e.g., D10A, aspartate to alanine) of SEQ ID NO: 5 (or the corresponding position of any of the proteins set forth in SEQ ID NOs: 6-261 and 264-816) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 protein cleaves a double stranded target nucleic acid) (see, for example, Jinek et al., Science. 2012 Aug. 17; 337(6096):816-21). See, e.g., SEQ ID NO: 262.

In some cases, a variant Cas9 protein can cleave the non-complementary strand of a target nucleic acid but has reduced ability to cleave the complementary strand of the target nucleic acid. For example, the variant Cas9 protein can have a mutation (amino acid substitution) that reduces the function of the HNH domain. Thus, the Cas9 protein can be a nickase that cleaves the non-complementary strand, but does not cleave the complementary strand. As a non-limiting example, in some embodiments, the variant Cas9 protein has a mutation at an amino acid position corresponding to residue H840 (e.g., an H840A mutation, histidine to alanine) of SEQ ID NO: 5 (or the corresponding position of any of the proteins set forth as SEQ ID NOs: 6-261 and 264-816) and can therefore cleave the non-complementary strand of the target nucleic acid but has reduced ability to cleave (e.g., does not cleave) the complementary strand of the target nucleic acid. Such a Cas9 protein has a reduced ability to cleave a target nucleic acid (e.g., a single stranded target nucleic acid) but retains the ability to bind a target nucleic acid (e.g., a single stranded target nucleic acid). See, e.g., SEQ ID NO: 263.

In some cases, a variant Cas9 protein has a reduced ability to cleave both the complementary and the non-complementary strands of a double stranded target nucleic acid. As a non-limiting example, in some cases, the variant Cas9 protein harbors mutations at amino acid positions corresponding to residues D10 and H840 (e.g., D10A and H840A) of SEQ ID NO: 5 (or the corresponding residues of any of the proteins set forth as SEQ ID NOs: 6-261 and 264-816) such that the polypeptide has a reduced ability to cleave (e.g., does not cleave) both the complementary and the non-complementary strands of a target nucleic acid. Such a Cas9 protein has a reduced ability to cleave a target nucleic acid (e.g., a single stranded or double stranded target nucleic acid) but retains the ability to bind a target nucleic acid. A Cas9 protein that cannot cleave target nucleic acid (e.g., due to one or more mutations, e.g., in the catalytic domains of the RuvC and HNH domains) is referred to as a "dead" Cas9 or simply "dCas9." See, e.g., SEQ ID NO: 264.

Other residues can be mutated to achieve the above effects (i.e. inactivate one or the other nuclease portions). As non-limiting examples, residues D10, G12, G17, E762, H840, N854, N863, H982, H983, A984, D986, and/or A987 of SEQ ID NO: 5 (or the corresponding mutations of any of the proteins set forth as SEQ ID NOs: 6-816) can be altered (i.e., substituted). Also, mutations other than alanine substitutions are suitable.

In some embodiments, a variant Cas9 protein that has reduced catalytic activity (e.g., when a Cas9 protein has a D10, G12, G17, E762, H840, N854, N863, H982, H983, A984, D986, and/or a A987 mutation of SEQ ID NO: 5 or the corresponding mutations of any of the proteins set forth as SEQ ID NOs: 6-816, e.g., D10A, G12A, G17A, E762A, H840A, N854A, N863A, H982A, H983A, A984A, and/or D986A), the variant Cas9 protein can still bind to target nucleic acid in a site-specific manner (because it is still guided to a target nucleic acid sequence by a Cas9 guide RNA) as long as it retains the ability to interact with the Cas9 guide RNA.

In addition to the above, a variant Cas9 protein can have the same parameters for sequence identity as described above for Cas9 proteins. Thus, in some cases, a suitable variant Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 4 motifs, each of motifs 1-4 having 60% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 70% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 75% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 80% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 85% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 90% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 95% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 99% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 100% amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable variant Cas9 protein comprises an amino acid sequence having 60% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 70% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 75% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 80% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 85% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 90% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 95% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 99% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 60% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 70% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 75% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 80% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 85% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 90% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 95% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 99% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 100% amino acid sequence identity to the Cas9 amino acid sequence set forth in SEQ ID NO: 5, or to any of the amino acid sequences set forth as SEQ ID NOs: 6-816.

Type V and Type VI CRISPR/Cas Endonucleases

In some cases, a suitable CRISPR/Cas effector polypeptide is a type V or type VI CRISPR/Cas endonuclease (i.e., the CRISPR/Cas effector polypeptide is a type V or type VI CRISPR/Cas endonuclease) (e.g., Cpf1, C2c1, C2c2, C2c3). Type V and type VI CRISPR/Cas endonucleases are a type of class 2 CRISPR/Cas endonuclease. Examples of type V CRISPR/Cas endonucleases include but are not limited to: Cpf1, C2c1, and C2c3. An example of a type VI CRISPR/Cas effector polypeptide is C2c2. In some cases, a suitable CRISPR/Cas effector polypeptide is a type V CRISPR/Cas endonuclease (e.g., Cpf1, C2c1, C2c3). In some cases, a Type V CRISPR/Cas effector polypeptide is a Cpf1 protein. In some cases, a suitable CRISPR/Cas effector polypeptide is a type VI CRISPR/Cas endonuclease (e.g., Casl3a).

Like type II CRISPR/Cas endonucleases, type V and VI CRISPR/Cas endonucleases form a complex with a corresponding guide RNA. The guide RNA provides target specificity to an endonuclease-guide RNA RNP complex by having a nucleotide sequence (a guide sequence) that is complementary to a sequence (the target site) of a target nucleic acid (as described elsewhere herein). The endonuclease of the complex provides the site-specific activity. In other words, the endonuclease is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the guide RNA.

Examples and guidance related to type V and type VI CRISPR/Cas proteins (e.g., Cpf1, C2c1, C2c2, and C2c3 guide RNAs) can be found in the art, for example, see Zetsche et al., Cell. 2015 Oct. 22; 163(3):759-71; Makarova et al., Nat Rev Microbiol. 2015 Nov. 13(11):722-36; Shmakov et al., Mol Cell. 2015 Nov. 5; 60(3):385-97; and Shmakov et al. (2017) *Nature Reviews Microbiology* 15:169.

In some cases, the Type V or type VI CRISPR/Cas endonuclease (e.g., Cpf1, C2c1, C2c2, C2c3) is enzymatically active, e.g., the Type V or type VI CRISPR/Cas polypeptide, when bound to a guide RNA, cleaves a target nucleic acid. In some cases, the Type V or type VI CRISPR/Cas endonuclease (e.g., Cpf1, C2c1, C2c2, C2c3) exhibits reduced enzymatic activity relative to a corresponding wild-type a Type V or type VI CRISPR/Cas endonuclease (e.g., Cpf1, C2c1, C2c2, C2c3), and retains DNA binding activity.

In some cases, a type V CRISPR/Cas endonuclease is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the Cpf1 amino acid sequence set forth in any of SEQ ID NOs:818-822.

In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the Cpf1 amino acid sequence set forth in any of SEQ ID NOs: 818-822.

In some cases, the Cpf1 protein exhibits reduced enzymatic activity relative to a wild-type Cpf1 protein (e.g., relative to a Cpf1 protein comprising the amino acid sequence set forth in any of SEQ ID NOs: 818-822), and retains DNA binding activity. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822; and comprises an amino acid substitution (e.g., a D→A substitution) at an amino acid residue corresponding to amino acid 917 of the Cpf1 amino acid sequence set forth in SEQ ID NO: 818. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822; and comprises an amino acid substitution (e.g., an E→A substitution) at an amino acid residue corresponding to amino acid 1006 of the Cpf1 amino acid sequence set forth in SEQ ID NO: 818. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822; and comprises an amino acid substitution (e.g., a D→A substitution) at an amino acid residue corresponding to amino acid 1255 of the Cpf1 amino acid sequence set forth in SEQ ID NO: 818.

In some cases, a suitable Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822.

In some cases, a type V CRISPR/Cas endonuclease is a C2c1 protein (examples include those set forth as SEQ ID NOs: 823-830). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 823-830. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c1 amino acid sequence set forth in any of SEQ ID NOs: 823-830.

In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c1 amino acid sequences set forth in any of SEQ ID NOs: 823-830). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c1 amino acid sequence set forth in any of SEQ ID NOs: 823-830. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c1 amino acid sequence set forth in any of SEQ ID NOs: 823-830. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c1 amino acid sequence set forth in any of SEQ ID NOs: 823-830.

In some cases, the C2c1 protein exhibits reduced enzymatic activity relative to a wild-type C2c1 protein (e.g., relative to a C2c1 protein comprising the amino acid sequence set forth in any of SEQ ID NOs: 823-830), and retains DNA binding activity. In some cases, a suitable C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 823-830.

In some cases, a type V CRISPR/Cas endonuclease is a C2c3 protein (examples include those set forth as SEQ ID NOs: 831-834). In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c3 amino acid sequence set forth in any of SEQ ID NOs: 831-834.

In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c3 amino acid sequence set forth in any of SEQ ID NOs: 831-834.

In some cases, the C2c3 protein exhibits reduced enzymatic activity relative to a wild-type C2c3 protein (e.g., relative to a C2c3 protein comprising the amino acid sequence set forth in any of SEQ ID NOs: 831-834), and retains DNA binding activity. In some cases, a suitable C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 831-834.

In some cases, a type VI CRISPR/Cas endonuclease is a C2c2 protein (examples include those set forth as SEQ ID NOs: 835-846). In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c2 amino acid sequence set forth in any of SEQ ID NOs: 835-846.

In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c2 amino acid sequence set forth in any of SEQ ID NOs: 835-846.

In some cases, the C2c2 protein exhibits reduced enzymatic activity relative to a wild-type C2c2 protein (e.g., relative to a C2c2 protein comprising the amino acid sequence set forth in any of SEQ ID NOs: 835-846), and retains DNA binding activity. In some cases, a suitable C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 835-846.

Examples and guidance related to type V or type VI CRISPR/Cas endonucleases (including domain structure) and guide RNAs (as well as information regarding requirements related to protospacer adjacent motif (PAM) sequences present in targeted nucleic acids) can be found in the art, for example, see Zetsche et al., Cell. 2015 Oct. 22; 163(3):759-71; Makarova et al., Nat Rev Microbiol. 2015 Nov. 13(11):722-36; Shmakov et al., Mol Cell. 2015 Nov. 5; 60(3):385-97; and Shmakov et al., Nat Rev Microbiol. 2017 Mar. 15(3):169-182; and U.S. patents and patent applications: 9,580,701; 20170073695, 20170058272, 20160362668, 20160362667, 20160298078, 20160289637, 20160215300, 20160208243, and 20160208241, each of which is hereby incorporated by reference in its entirety.

CasX and CasY Proteins

Suitable CRISPR/Cas effector polypeptides include CasX and CasY proteins. See, e.g., Burstein et al. (2017) Nature 542:237.

Dead CRISPR/Cas Effector Polypeptide-Fusion Proteins

In some cases, a CRISPR/Cas effector polypeptide suitable for use in a method of the present disclosure is an enzymatically inactive ("dead") CRISPR/Cas effector polypeptide that: i) retains the ability to bind a target nucleic acid when complexed with a guide RNA: and that ii) does not substantially cleave the target nucleic acid.

In some cases, a CRISPR/Cas effector polypeptide suitable for use in a method of the present disclosure is a fusion protein comprising: i) a dead CRISPR/Cas effector polypeptide; and ii) a transcriptional activator. Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

In some cases, a CRISPR/Cas effector polypeptide suitable for use in a method of the present disclosure is a fusion protein comprising: i) a dead CRISPR/Cas effector polypeptide; and ii) a transcriptional repressor. Examples of proteins (or fragments thereof) that can be used in decrease transcription include but are not limited to: transcriptional repressors such as the Kruppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

Guide RNA

A nucleic acid that binds to a class 2 CRISPR/Cas effector polypeptide (e.g., a Cas9 protein; a type V or type VI CRISPR/Cas protein; a Cpf1 protein; etc.) and targets the complex to a specific location within a target nucleic acid is referred to herein as a "guide RNA" or "CRISPR/Cas guide nucleic acid" or "CRISPR/Cas guide RNA." A guide RNA provides target specificity to the complex (the RNP complex) by including a targeting segment, which includes a guide sequence (also referred to herein as a targeting sequence), which is a nucleotide sequence that is complementary to a sequence of a target nucleic acid.

In some cases, a guide RNA includes two separate nucleic acid molecules: an "activator" and a "targeter" and is referred to herein as a "dual guide RNA", a "double-molecule guide RNA", a "two-molecule guide RNA", or a "dgRNA." In some cases, the guide RNA is one molecule (e.g., for some class 2 CRISPR/Cas proteins, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

In some cases, a guide RNA is introduced into a cancer cell and a non-cancerous cell of the same cell type as the cancer cell. In other instances, a nucleic acid comprising a nucleotide sequence encoding a guide RNA is introduced into a cancer cell and a non-cancerous cell of the same cell type as the cancer cell.

The nucleotide sequence encoding the guide RNA can be operably linked to a transcriptional control element(s). The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. The nucleotide sequence encoding the guide RNA can be operably linked to a promoter, where the promoter can be a constitutive promoter or a regulatable promoter (e.g., an inducible promoter). The nucleotide sequence encoding the guide RNA can be operably linked to a promoter (e.g., an inducible promoter), e.g., one that is operable in a cell type of choice (e.g., a mammalian cell, a human cell, a pancreatic cell, etc.).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a nucleotide sequence encoding a guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA in a eukaryotic cell it may sometimes be necessary to modify the sequence encoding the guide RNA to eliminate runs of Ts. In some cases, a nucleotide sequence encoding guide RNA is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions), and the like.

A nucleic acid comprising a nucleotide sequence encoding a guide RNA can be a recombinant expression vector. Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Nucleic Acid Sequencing

As summarized above, methods of the present disclosure, including e.g., those related to identifying biomarkers and molecular features of normal and cancer cells, may involve methods of nucleic acid sequencing to generate sequencing data, analysis of nucleic acid sequence data, classification of different cell types to generate cellular classification data, analysis of cellular classification data, processing of data (including e.g., sequencing data, cellular classification data, etc., and combinations of data) through computer algorithms to e.g., produce combinatorial gene expression signatures, identification of biomarkers and/or molecular cellular features (e.g., based on combinatorial gene expression signatures) relevant to cancer cells, and combinations thereof.

In some instances, methods of the present disclosure may involve nucleic acid sequencing to generate sequencing data. Expression analysis by sequencing may be achieved through the use of RNAseq technology directed at cellular mRNAs, including e.g., where mRNAs are preferentially targeted for amplification and/or sequencing, including but not limited to e.g., through the use of oligo-dT RT-PCR or other methods configured to preferentially amplify and/or sequence mRNAs.

In general, RNAseq involves the analysis of an RNA of interest, including an entire transcriptome or a portion thereof, utilizing one or more nucleic acid sequencing technologies. In some instances, single cell RNAseq (scRNAseq) may be employed, where RNAseq is performed on individual cells, in some instances, in multiplex fashion. Individual cells (i.e., single cells) for sequencing may obtained and/or isolated using a variety of methods, including limiting dilution, cell sorting (e.g., flow cytometry, microfluidics, etc.), multi-well-based systems, combinations thereof, and the like. RNA of interest (including from single or multiple cells) is generally amplified, in some instances following reverse transcription to DNA, prior to analysis using one or more nucleic acid sequencing methods.

Accordingly, in some cases, nucleic acid sequencing methods are utilized (e.g., for analysis of amplified nucleic acids, for obtainment of sequencing data, etc.), e.g., according to Second Generation (a.k.a. Next Generation or Next-Gen), Third Generation (a.k.a. Next-Next-Gen), or Fourth Generation (a.k.a. N3-Gen) sequencing technology protocols including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is commonly reverse transcribed to DNA before sequencing. However, in some instances, reverse transcription may not be necessary and RNA may be directly sequenced.

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotiter plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev. Microbiol., 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbiol., 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specific color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In some embodiments, nanopore sequencing (see, e.g., Astier et al., J. Am. Chem. Soc. 2006 Feb. 8; 128(5):1705-10, herein incorporated by reference) may be employed. The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In some embodiments, HeliScope by Helicos BioSciences (Voelkerding et al., Clinical Chem., 55: 641-658, 2009; MacLean et al., Nature Rev. Microbiol., 7: 287-296; U.S. Pat. Nos. 7,169,560; 7,282,337; 7,482,120; 7,501,245; 6,818,395; 6,911,345; 7,501,245; each herein incorporated by reference in their entirety) sequencing technology may be employed. Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics is used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

Other useful nucleic acid sequencing approaches include those developed by Stratos Genomics, Inc., including those involving the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Data Processing and Machine Learning

In some instances, methods of the present disclosure may involve analysis of nucleic acid sequence data. In some instances, in such analyses, sequencing data obtained from cancer cells may be compared to sequencing data obtained from normal cells. In some instances, in such analyses, sequencing data obtained from perturbed cancer cells, e.g., cancer cells contacted with a CRISPR/Cas system (as described above), may be compared to sequencing data obtained from non-perturbed cells, including non-perturbed cancer cells or non-perturbed normal cells. In some instances, in such analyses, sequencing data obtained from perturbed normal cells, e.g., normal cells contacted with a CRISPR/Cas system, may be compared to sequencing data obtained from non-perturbed cells, including non-perturbed cancer cells or non-perturbed normal cells. In some instances, perturbed cells may be compared to one another, e.g., perturbed cancer cells may be compared to corresponding perturbed normal cells, and the like.

Analysis of sequencing data may be performed at various levels and for various purposes. For example, in some instances, single cell analysis may be performed, where e.g., gene expression of single cells is analyzed through analysis of single cell sequencing data. Gene expression analysis performed may include differential expression analyses, where e.g., qualitative or quantitative differences in gene expression between cells or between cell populations may be compared. Accordingly, while in many instances analyses may be performed at the single cell level, in some instances groups or populations of cells may be analyzed together.

In some instances, methods of the present disclosure may involve classification of different cell types to generate cellular classification data. Any convenient and appropriate method of classification of different cell types may be employed. For example, in some instances, cells may be classified based on gene expression characteristics, including e.g., individual cell gene expression characteristics, differential expression characteristics (e.g., relative to other individual cells or relative to a relevant group or population of cells). In some instances, characteristics employed to classify cell types may be derived from the obtained expression data. For example, in some instances, machine learning, supervised or unsupervised, employing trained or untrained algorithms may be employed for cellular classification based on obtained expression data. Cells may be classified into various groups according to the classification scheme employed, including but not limited to e.g., wild-type (or normal) and cancerous, including but not limited to e.g., any of the cancers described herein. In some instances, cells may be classified according to a particular cancerous or non-cancerous cell type, including but not limited to e.g., tissues, organs, etc.

In some instances, methods of the present disclosure may involve analysis of cellular classification data. For example, following cellular classification, data pertaining to classified cells may obtained and further analyzed, e.g., to generate one or more useful statistics pertaining to one or more classified cell types. Useful statistics may include but are not limited to e.g., counts (e.g., the number of normal cells vs. abnormal cells; the number of detected cancer cells, the relative number of cells of particular cell types (including normal and cancerous cell types, etc.), averages, probabilities, sensitivity, specificity, likelihood analyses, and the like.

As summarized above, in some instances, methods of the present disclosure may involve one or more algorithms and the processing of data through computer algorithms. Various algorithms may be employed for various purposes, including but not limited to e.g., data manipulation/extraction, data conversion, data comparison, alignment, classification, clustering, and the like. Computer algorithms may be stored locally on a local computer memory or other computer readable medium or may be stored remotely, e.g., on a remote server accessible via the internet, including e.g., in cloud storage. Computer algorithms may be accessed and executed by a processor to perform the operations according to the instructions contained therein. Operations performed by a computer processor according to a subject algorithm may, depending on the process to be performed, be iterative or non-iterative.

As summarized above, systems of the present disclosure, subsystems (including algorithms), and/or data (including newly generated data and reference datasets) may be present on, transferred to, or otherwise accessible from one or more cloud platforms. A cloud platform may provide various computing functions, including but not limited to e.g., modular computing functions such as but not limited to e.g., computing functions and services, data storage functions and services, data analytic functions and services, machine learning functions and services, combinations thereof and the like. Other functionalities, and the means thereof, that may be present on a cloud platform may include database functions, networking functions, big data functions, AI functions, data management functions, cloud management functions, combinations thereof and the like. Essentially any component of the herein described systems and/or computational methods, the data therefor or produced therefrom, may be, in some instances, present on a cloud platform.

Figure 6A:
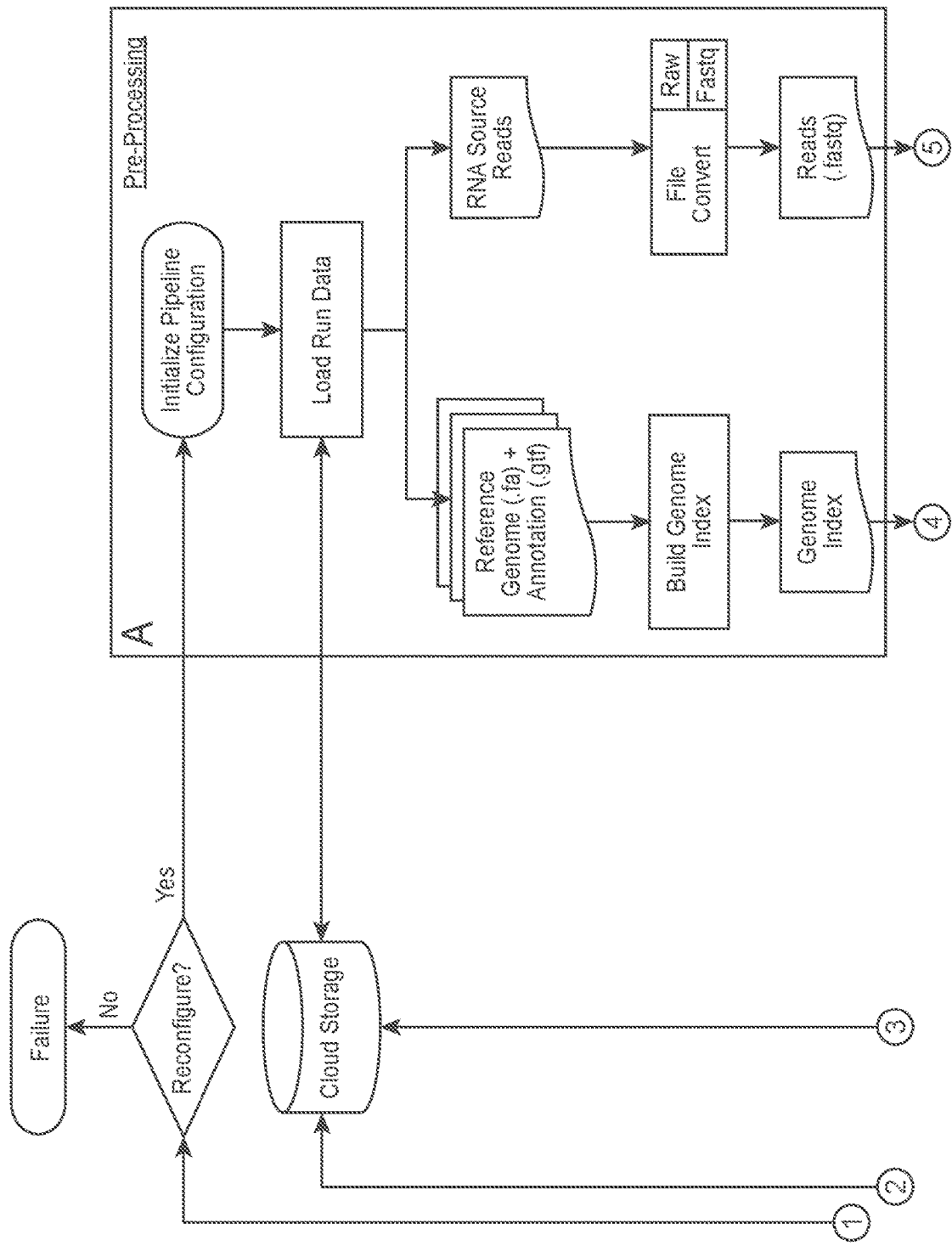
FIG. 6A-6C. Flowchart representation of the cloud functional genomics pipeline detailing steps in the (FIG. 6A) pre-processing, (FIG. 6B) alignment and expression extraction, and (FIG. 6C) downstream inference and analysis stages. Schematic depicting the architecture of a variable autoencoder network for latent, low-dimensional representation of RNA-seq profiles. The model is trained such that the decoder network component minimizes error in reconstructing full profiles from the low-dimensional representation.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the operations including: pre-processing functions, alignment and/or expression extraction functions, downstream inference and/or analysis functions, combinations thereof, and the like. In some instances, a system of one or more computers can be configured to perform particular operations or actions by virtue of having software, firmware, hardware, or a combination of them installed on the system that in operation causes or cause the system to perform one or more of the actions depicted in FIG. 6A-6C.

In some instances, systems and/or methods of the present disclosure may include one or more data pre-processing functions. For example, in some instances, pre-processing functions may include input from a user such as, e.g., a user may provide a file defining algorithm, or parameters thereof, to be employed in data processing. Such preprocessing information that may be provided by a user includes but is not limited to e.g., selection of an algorithm or pipeline configuration, selection and/or confirmation of algorithm or pipeline configuration parameters, initialization of an algorithm or pipeline, target identification parameters, target validation parameters, quality check parameters, data storage preferences, and the like.

Pre-processing will generally also involve the loading into memory of experimental and/or reference data to be used in the processing algorithm from local or remote sources. For example, sequence files, such as genome sequence files, annotation files, provided in any convenient and appropriate file format, such as but not limited to e.g., FASTA (.fa), gene transfer format (.gtf), and the like. Sources of such data may vary and may include local sources, such as but not limited to e.g., a computer readable medium attached to a computer housing the processor, or remote sources, such as internet-accessible sources including cloud-based locations.

File types may or may not be (and may or may not require) conversion prior to use in a subject algorithm. For example, in some instances, a raw file, such as raw sequencing reads, may be converted to another file type for use in the subject algorithm. Raw sequencing read files may vary and may include e.g., sequencing read archive (SRA) files, and the like. In instances were paired-end reads are employed, two raw read files may be provided and loaded into the subject algorithm (with or without conversion as appropriate), where each raw file represents reads from one end of the paired-end reads. Raw sequencing read files may be compressed or uncompressed; may contain various information, including but not limited to e.g., sequence identifier, sequence read, blank identifier, quality score, and the like; and may be readily converted between raw read file types into the file types employed in downstream processes. In some instances, an SRA file may be converted into a fastq file, using any convenient and appropriate conversion method, including but not limited to e.g., fastq-dump (available, along with various other useful software tools, at e.g., www(dot)ncbi(dot)nlm(dot)nih(dot)gov/sra/docs/toolkit-soft/).

Conversion of raw reads into a subsequent file type will generally facilitate further processing, such as processes that compare reads to reference data, such as but not limited to e.g., through various sequencing alignment algorithms. Such further processing may be performed following pre-processing as described herein.

Pre-processing may further involve the construction of one or more indexes employed in the subject algorithm. For example, in some instances, a reference index may be generated from two or more reference datasets, including but not limited to e.g., a genome dataset and an annotation dataset employed to generate a genome index. The combination of multiple datasets into a useful index may be achieved through various means, including but not limited to e.g., through the use of one or more bioinformatics toolkits, such as but not limited to e.g., the Spliced Transcripts Alignment to a Reference (STAR) Alignment Toolkit. In some instances, a useful index may be generated from a single dataset.

In some instances, systems and/or methods of the present disclosure may include one or more data alignment and/or expression extraction functions. Useful data alignment and/or expression extraction functions may include the alignment of sequencing data to reference data, e.g., for gene identification and/or quantification. In some instances, from aligned data, or data wherein the identities of reads have been otherwise obtained, expression data may be extracted, including but not limited to e.g., where such expression data indicates the relative expression of a gene relative to a reference standard or control, such as a control cell.

In data alignment and/or expression extraction functions, the resulting files from data pre-processing steps may be imported, or otherwise uploaded, into an alignment algorithm. Any convenient and appropriate alignment algorithm may be employed, including but not limited to e.g., the STAR Alignment algorithm. Such processes may, in some instances, designate the start of the alignment stage.

In some instances, alignment and/or expression extraction steps may also include one or more data quality checks. Useful data quality checks will vary and may e.g., evaluate various parameters of a produced alignment, including but not limited to e.g., percentage of mapped reads, uniquely mapped reads, and the like. Systems of the present disclosure may, e.g., in the event of a failed quality check, system crash, etc., may prompt a user for an input, e.g., a new data input, execution of further data checks, reconfiguration of algorithm and/or pipeline parameters, execution of an abort command, etc.

Produced alignments may or may not be converted into a different file type for further downstream processing. Useful file types for downstream processes will vary and may include but are not limited to e.g., Sequence Alignment Map (SAM)/Binary Alignment Map (BAM) file types, and the like. Generated alignments, converted or unconverted, may be stored locally, e.g., in system memory, or remotely, e.g., on a remote server. In some instances, features may be extracted from generated alignments, including expression counts, expression summaries (e.g., statistical summaries of expression), expression data normalization, and/or combinations thereof. For example, in some instances, normalized gene expression data, including expression counts and summation data, may be extracted and produced in an output in a file format useable by downstream processes, such as but not limited to e.g., a text or .cvs file format. In some instances, produced data, including e.g., data containing extracted expression features, may be loaded into, e.g., a machine learning algorithm, for further processing.

In some instances, a reference file type may be produced from the generated alignments, including modified and unmodified reference file types. For example, in some instances, a reference file type of alignment data may be produced, including but not limited to e.g., where the data is converted to more readily facilitate quantitative comparisons. Any convenient data conversion may be performed to generate a subject reference file, including but not limited to e.g., through the use of DESeq2 (see e.g., Love et al. *Genome Biol.* 2014; 15(12):55). Reference files may be generated and/or stored for various purposes including e.g., checking/testing of the parent dataset or other produced data, later downstream processes, later analysis, archival purposes, or the like. Such reference file types may be stored locally, e.g., on a local computer memory or other computer readable medium, or remotely, e.g., on a cloud-based storage system.

In some instances, systems and/or methods of the present disclosure may include one or more downstream inference and/or analysis stages. In some instances, downstream inference and analysis may involve quantification of generated and extracted expression features. Such quantification will vary and may be carried out using any convenient and appropriate approach, including but not limited to e.g., geometric methods; rank-order statistics; supervised machine learning methods; unsupervised clustering, deep learning methods, the like, or combinations thereof. For example, in some instances, extracted expression patterns may be quantified based on revision to wild-type expression patterns following genetic perturbation or overexpression. The extent of reversion to wild-type expression can be quantified in various ways, including but not limited to e.g., geometric methods; rank-order statistics; supervised machine learning methods; unsupervised clustering, deep learning methods (e.g., variational autoencoders (VAEs), generative models, etc.), the like, or combinations thereof.

In some instances, systems and/or methods of the present disclosure may employ one or more machine learning algorithms, one or more artificial neural networks, including e.g., where such function in a supervised or unsupervised manner e.g., variable autoencoder, manner. For example, in some instances, downstream inference and/or analyses employed in the subject methods may involve a machine learning algorithm configured to identify factors that differentiate two cell types, e.g., normal and cancer cells. Useful machine learning algorithms may, in some instances, be trained (e.g., trained such that the decoder network component minimizes error in reconstructing full profiles) or may, in some instances, be untrained.

Various statistical approaches may be applied in the models of the present methods and systems. In some instances, geometric methods may be applied. For example, in some instances, a standard distance metric may be applied, e.g., to determine the absolute or relative distance between transcriptional profiles, such as RNAseq and/or scRNAseq profiles. A non-limiting example of such a metric is the Euclidean distance, which here is defined as the L2 norm of the vector difference between two transcriptional profiles according to EQ. NO. 1 below:

$$\text{distance} = |B - A| = \sqrt{\sum_{i=1}^{N}(b_i - a_i)} \qquad \text{EQ. 1}$$

Where B and A are N-dimensional vectors representing two different transcriptomic profiles. As defined here, Euclidean distance is minimized for perturbations that maximally revert pancreatic cancer cells back to wild-type profiles.

In addition to Euclidean distance, the cosine distance between profiles may also be measured, in some instances, and such is defined in EQ NO. 2 below:

$$\text{cosine distance} = 1 - \cos\theta = 1 - \frac{A \cdot B}{|A||B|} \quad \text{EQ. 2}$$

Where θ is the angle between the vector representations of two profiles to be compared, denoted as A and B. In some cases, it may be necessary to normalize or re-weight gene reads prior to calculation of the Euclidean or cosine distance, especially if certain genes are to be prioritized.

In some instances, rank-order statistics may be employed, e.g., to measure transcriptional reversion. For example, in some instances, the absolute expression rank for each gene may be calculated from averaged RNA-seq measurements of perturbed cells (e.g., cancer cells).

In some instances, an enrichment statistic, such as Kolmogorov-Smirnov statistic, may be calculated, including e.g., where such statistic is calculated for genes within the perturbed sample that are differentially expressed by at least twofold between unperturbed wild-type and cancer cells.

In some instances, differentially expressed genes may be identified from bulk-averaged measurements, including e.g., bulk-averaged measurements of unperturbed cancer or wild-type cells (such as but not limited to e.g., ductal or acinar cells). Summarization of the enrichment statistics, analogous to the approach used in Subramanian et al. ((2017) *Cell* 171:1437) or Chen et al. ((2017) *Nat. Commun.* 8:16022), facilitate identification of perturbations that maximally revert cancer cells to wild-type cells.

In some instances, a model trained on unperturbed cells may be applied to sequencing profiles from perturbed samples and employed to classify cells and/or samples as wild-type or diseased. In some embodiments, perturbations that maximally revert cancer cells back to wild-type expression levels will result in a greater degree of "wild-type" classifications by the trained model.

In some instances, soft probabilistic labels from a supervised machine learning model may be used instead of hard class labels. For example, in some instances, soft vs. hard labels may be used in order to assess the extent of reversion of expression toward wild-type levels after perturbation. In some instances, the distributions of positive class probabilities for wild-type, cancer, and perturbed cells are compared. Probability distributions may be compared qualitatively or quantitatively such as with a student's t-test in order to identify perturbations that maximally revert class probabilities towards the wild-type distribution.

In some instances, systems and methods of the present disclosure may include reducing the dimensionality of transcriptomic profiles. For example, in some instances, before performing supervised classification, dimensionality of transcriptomic profiles may be reduced, in order to improve the performance of machine learning models. In some instances, reduction of dimensionality may not be performed. Dimensionality reduction may be achieved, in some instances, via one of several methods, including but not limited to e.g.: a) principal component analysis (PCA, either linear or kernel-based), non-negative matrix factorization (NMF), linear discriminant analysis (LDA), recursive feature elimination, or deep learning methods such as variable autoencoders (VAE, see: Xie et al. ((2017) *BMC Genomics* 18:845)). These various methods may be, in some instances, executed with sklearn and TensorFlow in Python or caret in R.

In some instances, a variable autoencoder may be employed during inference and analysis process of the systems and/or methods of the present disclosure. An autoencoder is a type of artificial neural network used in machine learning to develop efficient data codings in an unsupervised manner. A variational autoencoder may employ models that inherit autoencoder architecture and make further assumptions concerning the distribution of latent variables.

Figure 6B:
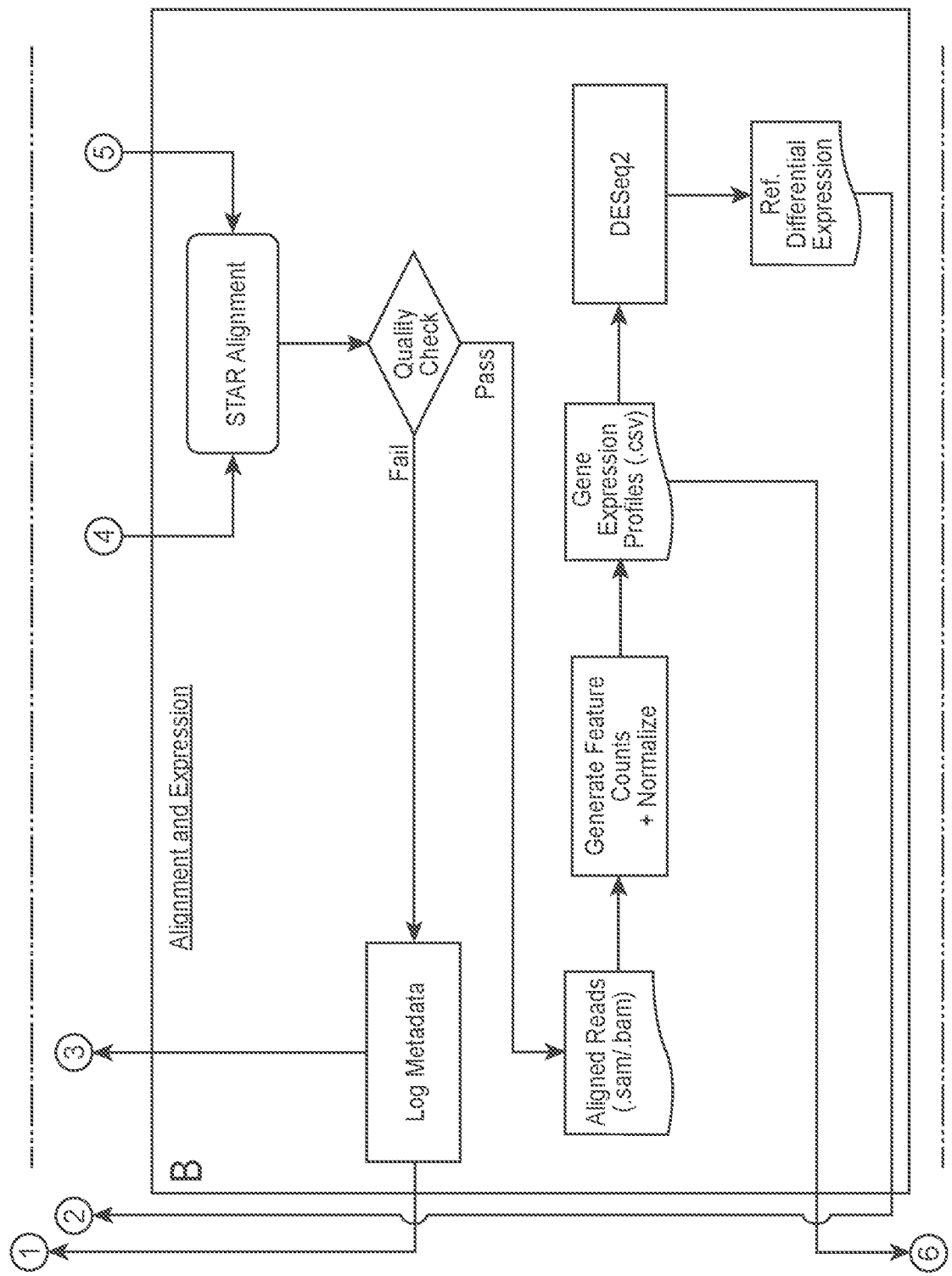
Figure 6C:
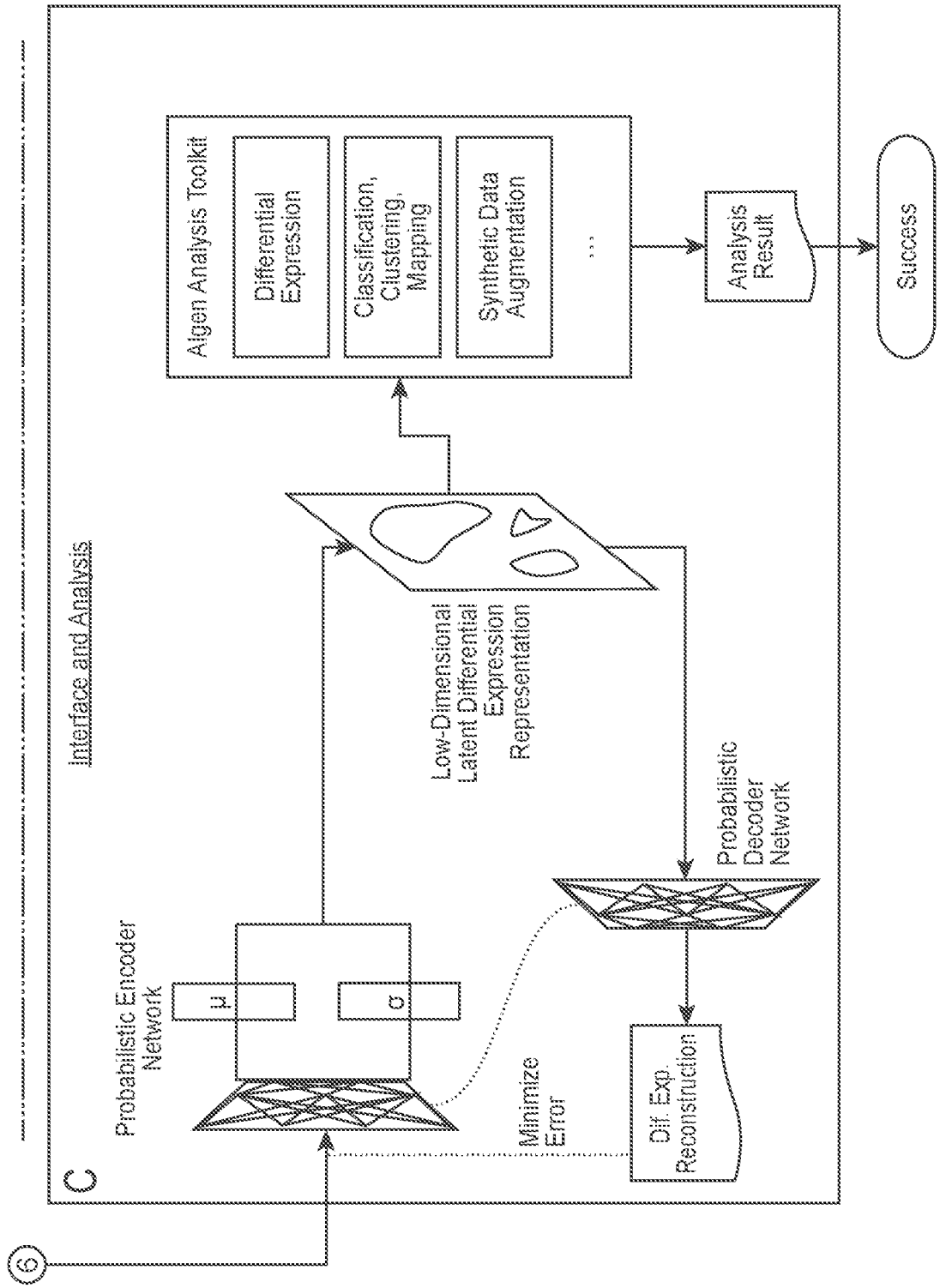

In some instances, a systems and methods of the present disclosure may employ a variable autoencoder as depicted in FIG. 6C. As depicted, vector representations of gene expression data from sequencing profiles (e.g., scRNAseq profiles) are used as inputs to train a coupled encoder/decoder network, which attempt to minimally and accurately represent the information content within RNA-seq profiles in a latent, low-dimensional space via non-linear feature reduction. In some embodiments, the model is trained such that the networks minimize error in reconstructing full profiles from the low-dimensional encoding.

In some instances, clustering methods may be employed in the one or more downstream inference and/or analysis stages of the present methods and/or systems. Useful clustering methods may be supervised or unsupervised as appropriate and desired. For example, in some cases, reversion of gene expression to wild-type levels is assessed via unsupervised clustering methods. In this approach, vector representations of RNA-seq profiles for wild-type, cancer, and perturbed cells are clustered. Perturbations that result in enrichment within the wild-type cluster are selected for further therapeutic development.

Clustering may be performed using any convenient and appropriate algorithm, the selection of which will vary. For example, in some instances clustering may be performed with one or more of several algorithms, including, but not limited to: k-means, fuzzy C means clustering, density-based methods such as DBSCAN, or modern methods such as SC3 (Kiselev et al. (2017) *Nat. Commun.* 14:483). Enrichment may be, in some instances, defined in terms of the fraction of perturbed cells that co-cluster with the majority cluster for wild-type cells. In some cases, enrichment towards the wild-type cluster is assessed geometrically via the distance metrics outlined herein.

Where employed, dimensionality reduction may be performed at any convenient and appropriate point in a subject procedure. For example, in some instances, dimensionality reduction may be performed prior to clustering to reduce statistical noise. In addition to the methods for dimensionality reduction discussed herein, clustering may, in some instances, also be performed on the pairwise Euclidean or cosine distance between profiles, the pairwise Pearson or Spearman correlation coefficient between profiles, or on the enrichment statistic summarizations discussed herein.

In some instances, an inference and downstream analysis workflow as depicted in FIG. 6C may be employed. For example, in some instances, a generative model that takes as input vector representations of gene expression data from single-cell RNA-seq profiles, and uses variational inference and stochastic optimization for deep neural networks to approximate the parameters that govern the distribution of expression values of each gene in every cell, using a non-linear mapping between observations and a low-dimensional latent space may be employed. Such a process pools information between similar cells or genes while taking nuisance factors of variation such as batch effects and limited sensitivity into account.

As depicted, the algorithm trains a coupled set of encoder/decoder networks, which attempt to minimally and accurately represent the information content within RNA-seq profiles in a latent, low-dimensional space via non-linear feature reduction. The model is trained such that the networks minimize error in reconstructing full profiles from the low-dimensional encoding, a process mathematically equivalent to retaining maximal differentiation between different profiles in the latent space.

The procedures described herein may, in some instances, provide for certain advantages, examples of which are described herein and not intended to be limiting. For example, in addition to enabling differential expression analysis to be conducted by quantifying and accentuating the differentially expressed genes, the resulting latent space mapping serves as a tool for a plethora of downstream analyses. For example, with regards to classification and clustering, the networks are optimized to keep different profiles in the latent space maximally differentiated, encoding a new observation can provide a more precise notion of cell identity over generic clustering methods, which often suffer from significant cluster overlapping. With regards to transition analysis, the latent space is constructed to be continuous such that an inferred non-linear interpolation between any two sample points in the space also exists in the space. This facilitates mapping a continuous notion of identity between core representations, for instance, diseased and non-diseased cells, detailing an interpolated and smooth transition between the two states. With regards to synthetic data augmentation, the latent space is truly continuous, thus it was possible to generate a complete gene expression profile from any given point in the latent space by extrapolating via the tuned decoder network. For instance, extrapolation of the expression of an observation between two recorded observations, a totally healthy and totally diseased cell to obtain the expression profile of a "half" diseased cell by the definition of the latent space can be performed, retaining the underlying expression patterns of the space.

In some instances, e.g., in the case of supervised machine learning, the collection of sequencing profiles from unperturbed wild-type and cancer cells may be combined and split into cell-type-stratified train and test datasets via random indexing. In a non-limiting example, the train dataset may comprise on the order of 70% of all profiles, while the test dataset may comprise on the order of 30% of all profiles. A supervised machine learning model may then be trained for maximal accuracy to discriminate between wild-type versus cancer cells based on vector representations of single-cell measurements.

Figure 7:
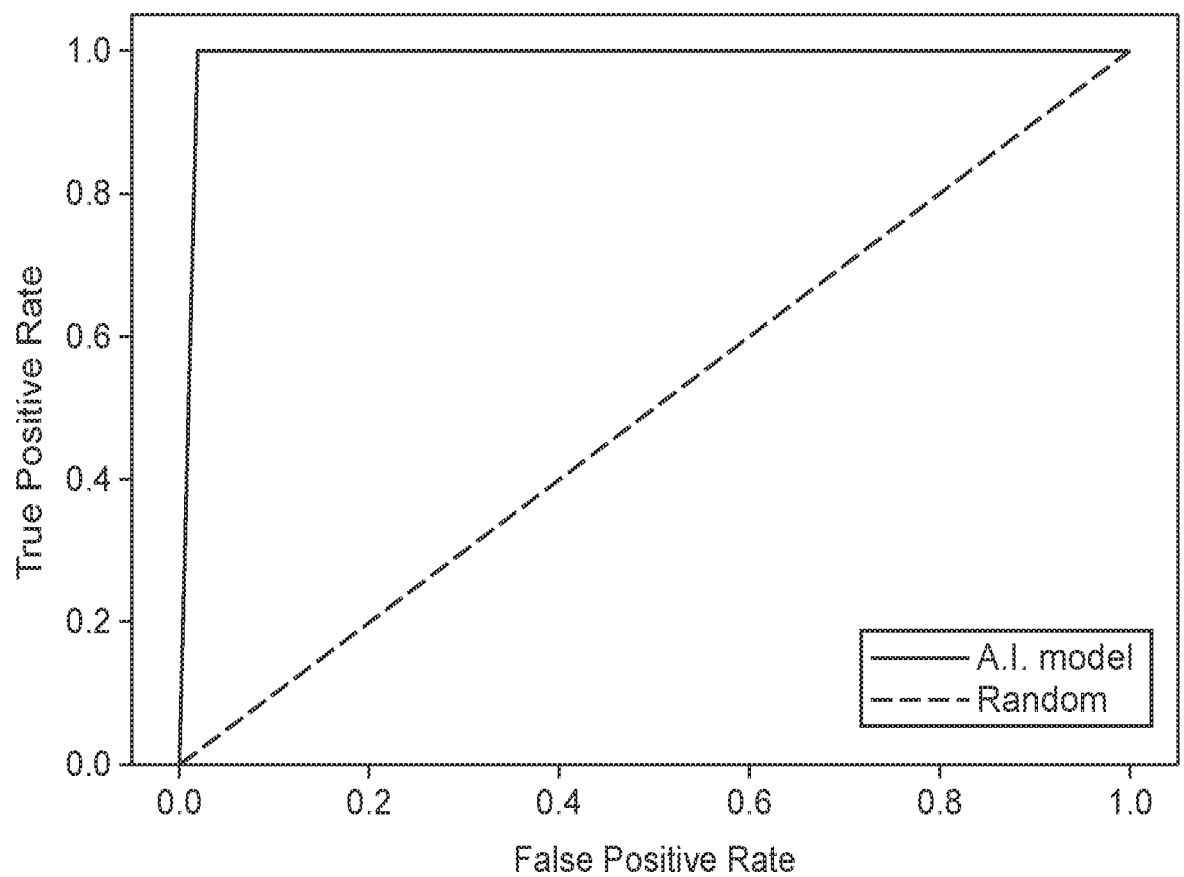
FIG. 7. Machine learning to identify perturbations (biomarkers) that revert cancer cell transcriptomes towards wild-type expression patterns. Example demonstrating the use of a Random Forest classifier to discriminate between wild-type and cancer cells based on RNA-seq expression profiles. A sample of 2,000 single-cell RNA-sequencing profiles (equal mixture of cancer and wild-type) were used to train a Random Forest in sklearn. The receiver operating characteristic curve reveals that the machine learning model discriminated between pancreatic cancer and ductal cells within the holdout set with >99.5% accuracy.

In various instances, applicable machine learning models include, but are not limited to: Random Forest, Gradient Boosting, logistic and linear regression, and convolutional neural networks (CNNs). In some instances, data splitting and model training is performed, including e.g., where data splitting and model training are readily performed through the use of e.g., open-source packages such as sklearn and TensorFlow in Python or caret in R. For CNNs, a minimal network consisting of an input layer, a convolutional layer with three different filter sizes, a max pooling layer, and an activation layer may be constructed in TensorFlow to classify unperturbed cells as wild-type or cancer based on this input representation. A non-limiting example of supervised classification to discriminate between wild-type and cancer cells is depicted in FIG. 7.

In some instances, methods of the present disclosure may involve combinatorial gene expression signatures and/or result in the production of combinatorial gene expression signatures. In general, a combinatorial gene expression signature may represent a collection of genes expressed at relative levels that collectively correspond to a particular cellular classification, including those generated using the machine learning algorithms described herein. For example, in some instances, analysis of cellular classification data may allow for the construction of a combinatorial gene expression signature that may prospectively identify a particular cell type, e.g., based on measuring the gene expression of the cell. As such, a combinatorial gene expression signature may be useful in identifying a cell, e.g., as a normal cell, as a cancer cell, etc., based on measured expression in the cell. The number of different genes included in a particular combinatorial gene expression signature may vary and may range from 2 to 100 or more, including but not limited to e.g., 2 to 100, 2 to 75, 2 to 50, 2 to 25, 2 to 20, 2 to 15, 2 to 10, 2 to 5, 5 to 100, 5 to 75, 5 to 50, 5 to 25, 5 to 20, 5 to 15, 5 to 10, 10 to 100, 10 to 75, 10 to 50, 10 to 25, 10 to 20, 10 to 15, 15 to 100, 15 to 75, 15 to 50, 15 to 25, 15 to 20, etc.

In some instances, methods of the present disclosure may involve identification of biomarkers and/or molecular cellular features relevant to cancer cells. In some instances, identification of biomarkers and/or molecular cellular features may be based on combinatorial gene expression signatures, as described herein. In some instances, combinatorial gene expression signatures may include identified biomarkers and/or identified molecular cellular features, as described herein.

Target Genes

As discussed above, the present disclosure provides methods of identifying a target or combinatorial targets for cancer treatment. Examples of such targets, identified using a method of the present disclosure, are depicted in FIG. 8.

For example, in some cases, a gene product (an mRNA and/or a polypeptide) that is up-regulated (produced at a higher level; e.g., at a level that is at least 10%, at least 25%, at least 50%, at least 75%, at least 100%, at least 2.5-fold, at least 5-fold, at least 10-fold, or more than 10-fold higher) in cancer cells (e.g., in cancerous ductal and acinar cells) compared to the level of the gene product in a non-cancerous cell of the same cell type (e.g., in non-cancerous ductal and acinar cells), is selected from: Ddit4, Cdkn2a, Hk2, Hes1, Asns, Galk1, Shmt2, Cct8, Gars, Psph, Ppid, Ruvbl1, Chchd4, Nop16, Eif4ebp1, Gcsh, Ddx21, Ino80e, Tomm70a, Bri3 bp, Mpp6, Tomm20, Nhp2l1, Akr1b3, Noc2l, Nolc1, Tomm5, Nhp2, Rsl24d1, Hnrnpdl, Dnajc2, Hacd1, Ddx3x, Mat2a, Ddx46, Gm16286, Tpi1, Gcat, Nmt1, Jun, Cbx3, Id3, Fam3c, Pcbp4, Id1, Mt2, Bcat1, Sparc, Pcolce, Ifitm3, S100a4, Xist, Tnfrsf26, Dusp9, Ly6a, Ccnd2, Emp3, Prkg2, and Ndn.

As another example, in some cases, a gene product (an mRNA and/or a polypeptide) that is down-regulated (produced at a lower level; e.g., at a level that is at least 10%, at least 15%, at least 20%, at least 25%, at least 30%, at least 35%, at least 40%, at least 45%, at least 50%, at least 60%, at least 70%, at least 80%, or at least 90% lower) in cancer cells (e.g., in cancerous ductal and acinar cells) compared to the level of the gene product in a non-cancerous cell of the same cell type (e.g., in non-cancerous ductal and acinar cells), is selected from: Gm10116, Pcbd1, Gamt, Gstm1, Chchd10, Dlk1, Sod3, Bst1, Krt7, Anxa8, Slpi, Sorbs2, Ankrd1, Msln, Klra4, Igfbp7, Gm10709, Tspan8, Gjb4, Anxa3, Krt19, Krt18, Akap12, Cdc42ep5, Tubb2a, Fbln2, Cyba, Timp3, Ucp2, Sgk1, Tubb2b, Fads3, H2-K1, Trp53, Spint2, Lsr, Prss2, Kcnk3, Vtn, Chga, Cpa1, Tm4sf4, Gc, Reg1, Try5, Ctrb1, Nts, Mdk, Bex2, Nkx6-2, Resp18, Cldn10, Penk, D930028M14R, Cela1, Rbp4, Bex4, Sepp1, Mest, Apoe. Nucleotide sequences of such gene products (where the gene product is an mRNA) and amino acid sequences of such gene products (where the gene product is a polypeptide) are known in the art. For example, nucleotide sequences and amino acid sequences of such gene products can be found at genecards(dot)org and at ncbi(dot)nlm(dot)nih(dot)gov.

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure numbered 1-24 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A method for identifying a target or combinatorial targets for cancer treatment, the method comprising:
  (a) introducing into a cancer cell and into a corresponding normal cell of the same cell type as the cancer cell a CRISPR/Cas system comprising
    i) a CRISPR/Cas effector polypeptide; and
    ii) a CRISPR/Cas guide RNA, or a nucleic acid comprising a nucleotide sequence encoding the CRISPR/Cas guide RNA, wherein the CRISPR/Cas guide RNA targets a gene of interest, thereby reducing expression of the target gene, wherein said introducing results in a modified normal cell and a modified cancer cell;
  (b) monitoring one or more molecular features and/or phenotypes in the modified normal cell and the modified cancer cell following reduction of target gene expression, using a computer algorithm, thereby generating data relating to the one or more molecular features and/or phenotypes; and
  (c) where the one or more molecular feature and disease phenotype indicates a reduction in the cancerous state of the cancer cell, identifying the target gene as a candidate cancer treatment target or combinatorial targets.

Aspect 2. The method of aspect 1, wherein the CRISPR/Cas effector polypeptide is a fusion protein comprising: i) an enzymatically inactive CRISPR/Cas effector polypeptide; and ii) a transcriptional inhibitor.

Aspect 3. The method of aspect 1, wherein the CRISPR/Cas effector polypeptide is a fusion protein comprising: i) an enzymatically inactive CRISPR/Cas effector polypeptide; and ii) a transcriptional activator.

Aspect 4. The method of aspect 1, wherein the CRISPR/Cas effector polypeptide is enzymatically active, and wherein step (b) comprises introducing two CRISPR/Cas guide RNAs.

Aspect 5. The method of any one of aspects 1-4, wherein the normal cell is a non-cancerous pancreatic cell, and the cancerous cell is a pancreatic cancer cell.

Aspect 6. The method of any one of aspects 1-4, wherein the normal cell is a non-cancerous brain cell, and the cancerous cell is a brain cancer cell.

Aspect 7. The method of any one of aspects 1-4, wherein the normal cell is a non-cancerous ovarian cell, and the cancerous cell is an ovarian cancer cell.

Aspect 8. The method of any one of aspects 1-4, wherein the normal cell is a non-cancerous breast cell, and the cancerous cell is a breast cancer cell.

Aspect 9. The method of any one of aspects 1-4, wherein said monitoring comprises assessing expression levels of one or more indicator genes in the normal and the cancerous cell.

Aspect 10. The method of any one of aspects 1-4, wherein said monitoring comprises assessing morphological features of the normal and the cancerous cell.

Aspect 11. The method of any one of aspects 1-4, wherein said monitoring comprises sequencing RNA obtained from the modified normal cell and the modified cancer cell, to obtain sequence data.

Aspect 12. The method of aspect 11, wherein the sequencing is single-cell RNA sequencing.

Aspect 13. The method of aspect 11 or aspect 12, further comprising analyzing the sequence data.

Aspect 14. The method of aspect 13, wherein said analysis comprises use of an algorithm stored on a computer-implemented system to compare the data from the modified normal cell and the modified cancer cell.

Aspect 15. The method of aspect 11 or aspect 12, further comprising storing the sequence data in a computer database.

Aspect 16. The method of aspect 11 or aspect 12, further comprising cloud storage of the sequence data.

Aspect 17. The method of any one of aspects 1-16, comprising comparing the molecular feature or phenotype to a reference molecular feature or phenotype.

Aspect 18. The method of any one of aspects 1-17, further comprising implementing one or more data alignment and/or expression extraction functions to analyze the molecular feature and/or phenotype data.

Aspect 19. The method of aspect 18, wherein said data alignment is carried out using a STAR Alignment algorithm.

Aspect 20. The method of aspect 18 or 19, comprising one or more data quality checks.

Aspect 21. The method of any one of aspects 18-20, further comprising producing a reference file type from the alignment.

Aspect 22. The method of any one of aspects 1-21, further comprising one or more downstream inference and/or analysis steps to process the data.

Aspect 23. The method of aspect 22, wherein said downstream inference and/or analysis comprises one or more of a geometric method, rank-order statistics, a supervised machine learning method, unsupervised clustering, and a deep learning method.

Aspect 24. A method of identifying biomarkers and molecular features of normal and cancer cells, the method comprising:
  (a) single-cell RNAseq (scRNAseq) analysis of normal and cancer cells;
  (b) analyzing the single-cell RNAseq on a cloud platform;
  (c) classifying different types of cells;
  (d) developing computer algorithms; and
  (e) identifying biomarkers and molecular features of normal and cancer cells.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Materials and Methods

Generation of CRISPRi (CRISPR Interference) Cell Lines and Libraries

To produce CRISPRi cell lines, the murine pancreatic cancer cells KRPC (Lito et al. ((2014) Cancer Cell 25:697) were transduced with a plasmid (Addgene Plasmid #85969, Adamson et al. ((2016) Cell 167:1867) expressing catalytically dead Cas9 fused to a transcriptional repressor peptide KRAB (dCas9-KRAB). The BFP+ cells were then sorted by flow cytometry. A custom sgRNA CRISPRi library focused on 34 drug target genes (two sgRNA per gene) was designed and constructed as previously described (Adamson et al. 2016, supra).

Molecular Profiling of Cells by Single-Cell RNAseq (scRNAseq)

~17,400 the murine pancreatic cancer cells (over 95% viability) were loaded to Chromium Single Cell 3' Chip and separated via 1 channel into droplet emulsion using the Single Cell 3' Reagent Kits v2 following manufacturer's instructions (10× Genomics). The single-cell RNAseq (scRNAseq) libraries were prepared according to the manufacturer's instructions (10× Genomics), and paired-end sequenced using one lane of the HiSeq 4000 Sequencing System (Illumina). The transformed acinar cells (266-6 cells) and murine ductal cells were analyzed following the same methods. To generate the murine pancreatic cancer cells with a custom CRISPRi library, lentivirus of individual sgRNA within the library was first produced separately. Then the individual sgRNA lentiviruses were first combined into a complete lentivirus library pool, and the library was transduced into the cells using conditions that predominantly lead to a single lentiviral integration and represent each sgRNA in a calculated number of at least 1000 cells. Transduced cells were selected by 2 µg/mL puromycin for 3 d; at each passage, >20 million cells were maintained to preserve library representation throughout the experiment. ~17,400 the murine pancreatic cancer cells with the CRISPRi library (over 95% viability) were analyzed on day 5 after lentiviral infection according to the abovementioned method.

Suppression of Target Gene by CRISPRi

Cells expressing dCas9-KRAB were transduced with BFP-linked sgRNAs (Addgene Plasmid #85967, Adamson et al. 2016, supra) targeting candidate genes. The transduced cells were then selected by puromycin for 3 days and the BFP+ cells were collected on day for analysis. Total mRNA was isolated using Oligotex mRNA Mini Kit (Qiagen) following manufacturer's instructions. cDNA synthesis and qRT-PCR were performed using SuperScript VILO Master Mix (Thermo Fisher Scientific) and DyNAmo HS SYBR Green qPCR Kits (Thermo Fisher Scientific), respectively. Quantitative PCR analysis was performed on a QuantStudio™ 5 Real-Time PCR System (Thermo Fisher Scientific). All signals were normalized to the levels of β-actin and were quantified using the deltaCt method. Every reaction was performed in triplicate using gene-specific primers.

Assay for Validation of Target Gene by CRISPRi

Cells expressing dCas9-KRAB were transduced with BFP-linked sgRNAs (Addgene Plasmid #85967, Adamson et al. Cell 2016) targeting candidate genes. BFP+ cells were mixed with untransduced cells at around 1:1 ratio and subsequently cultured. The percentage of BFP+(sgRNA expressing) cells was determined by Attune NxT Flow Cytometer (Thermo Fisher Scientific) at different time points. Changes (relative to day 0) were used as readout of the growth inhibitory effects.

Cloud Functional Genomics Pipeline, Pre-Processing, Alignment, and Expression Quantification In pre-processing (FIG. 6A), the pipeline is configured with a user provided file that determines algorithms to be used in various stages of the pipeline, in addition to a set of parameters specifying particular quality checks and storage preferences. A set of raw reads, .fa reference genome files, and .gtf annotation files are loaded into memory from cloud storage. Raw read data is converted to the fastq file format via fastq-dump in the SRA Toolkit. The reference genome and annotation file are used to construct a genome index via the STAR Alignment Toolkit. The resulting files from these two steps are fed into the STAR Alignment algorithm in the start of the alignment stage (FIG. 6B). Once alignment has finished, if the resulting alignment passes a series of predetermined quality checks examining metrics such as the percentage of mapped reads and uniquely mapped reads, it is then stored locally as a .sam/.bam aligned file. If the program crashes, or the resulting alignment does not pass the required quality checks, the bioinformatician is prompted to check the data, reconfigure the pipeline, or abort. The aligned file is then passed to featureCounts to obtain read summarization data, and normalized to obtain gene expression data in csv format. A reference differential expression file is computed using DESeq2 for sanity checking and testing in the downstream analysis stage.

Statistical Analysis of Perturbed Cells

Gene-aligned, single-cell RNA profiles of pancreatic cancer cells are quantified based on their reversion to wild-type expression patterns following gene knockout, gene repression, or gene activation via the methods described above (CRISPR, CRISPRi, or CRISPRa, respectively). In principle, extent of reversion to wild-type expression can be quantified via several ways, including but not limited to: a) geometric methods; b) rank-order statistics; c) supervised machine learning methods; d) unsupervised clustering; or e) deep learning methods such as variational autoencoders (VAEs) and generative models. In some cases, different methods are applied in combination to generate a quantitative measure of reversion to wild-type expression levels.

In the case of geometric methods, a standard distance metric is applied to determine the absolute or relative distance between scRNA-seq transcriptional profiles. One such metric is the Euclidean distance, which here is defined as the L2 norm of the vector difference between two transcriptional profiles according to EQ. NO. 1 below:

$$\text{distance} = |B - A| = \sqrt{\left(\sum\_(i = 1)^\wedge N(b\_i - a\_i)\right)} \quad \text{EQ. 1}$$

Where B and A are N-dimensional vectors representing two different transcriptomic profiles. As defined here, Euclidean distance is minimized for perturbations that maximally revert pancreatic cancer cells back to wild-type profiles.

In addition to Euclidean distance, the cosine distance between profiles is also measured and is defined in EQ NO. 2 below:

$$\text{cosine distance} = 1 - \cos\theta = 1 - (A \cdot B)/|A||B| \quad \text{EQ. 2}$$

Where θ is the angle between the vector representations of two profiles to be compared, denoted as A and B. In some cases, it may be necessary to normalize or re-weight gene reads prior to calculation of the Euclidean or cosine distance, especially if certain genes are to be prioritized.

In the case of rank-order statistics to measure transcriptional reversion, the absolute expression rank for each gene is calculated from averaged RNA-seq measurements of perturbed (e.g., CRISPR, CRISPRi, CRISPRa) cancer cells. An enrichment statistic, such as Kolmogorov-Smirnov statistic, is calculated for genes within the perturbed sample that are differentially expressed by at least twofold between unperturbed wild-type and cancer cells. In practice, differentially expressed genes are identified from bulk-averaged measurements of unperturbed pancreatic cancer or wild-type (e.g. ductal or acinar) cells. Summarization of the enrichment statistics, analogous to the approach used in Subramanian et al. 2017, supra, or Chen et al. 2017, supra, would allow for identification of perturbations that maximally revert cancer cells to wild-type cells.

The model trained on unperturbed cells is then applied to scRNA-seq profiles from perturbed samples in order to classify them as wild-type or diseased. In principle, perturbations that maximally revert cancer cells back to wild-type expression levels will result in a greater degree of "wild-type" classifications by the trained model.

In some cases, the soft probabilistic labels from the supervised machine learning model may be used instead of the hard class labels in order to assess the extent of reversion of expression toward wild-type levels after perturbation. In this scenario, the distributions of positive class probabilities for wild-type, cancer, and perturbed cells are compared. Probability distributions may be compared qualitatively or quantitatively such as with a student's t-test in order to identify perturbations that maximally revert class probabilities towards the wild-type distribution.

In some cases, it may be necessary to reduce the dimensionality of transcriptomic profiles before performing supervised classification in order to improve the performance of machine learning models. Dimensionality reduction is achieved via one of several methods, including: a) principal component analysis (PCA, either linear or kernel-based), non-negative matrix factorization (NMF), linear discriminant analysis (LDA), recursive feature elimination, or deep learning methods such as variable autoencoders (VAE, see: Xie et al. ((2017) *BMC Genomics* 18:845)). These various methods are executed with sklearn and TensorFlow in Python or caret in R.

A schematic for the design of a variable autoencoder is depicted in FIG. 6C. Vector representations of gene expression data from scRNAseq profiles are used as inputs to train a coupled encoder/decoder network, which attempt to minimally and accurately represent the information content within RNA-seq profiles in a latent, low-dimensional space via non-linear feature reduction. The model is trained such that the networks minimize error in reconstructing full profiles from the low-dimensional encoding.

In some cases, reversion of gene expression to wild-type levels is assessed via unsupervised clustering methods. In this approach, vector representations of RNA-seq profiles for wild-type, cancer, and perturbed cells are clustered. Perturbations that result in enrichment within the wild-type cluster are selected for further therapeutic development. Clustering is performed with one of several algorithms, including, but not limited to: k-means, fuzzy C means clustering, density-based methods such as DBSCAN, or modern methods such as SC3 (Kiselev et al. (2017) *Nat. Commun.* 14:483). Here, enrichment is defined in terms of the fraction of perturbed cells that co-cluster with the majority cluster for wild-type cells. In some cases, enrichment towards the wild-type cluster is assessed geometrically via the distance metrics outlined above.

In some cases, dimensionality reduction is performed prior to clustering to reduce statistical noise. In addition to the methods for dimensionality reduction discussed above, clustering may also be performed on the pairwise Euclidean or cosine distance between profiles, the pairwise Pearson or Spearman correlation coefficient between profiles, or on the enrichment statistic summarizations discussed above.

Example 2: Molecular Profiling by Single-Cell RNAseq (scRNAseq

Figure 2:
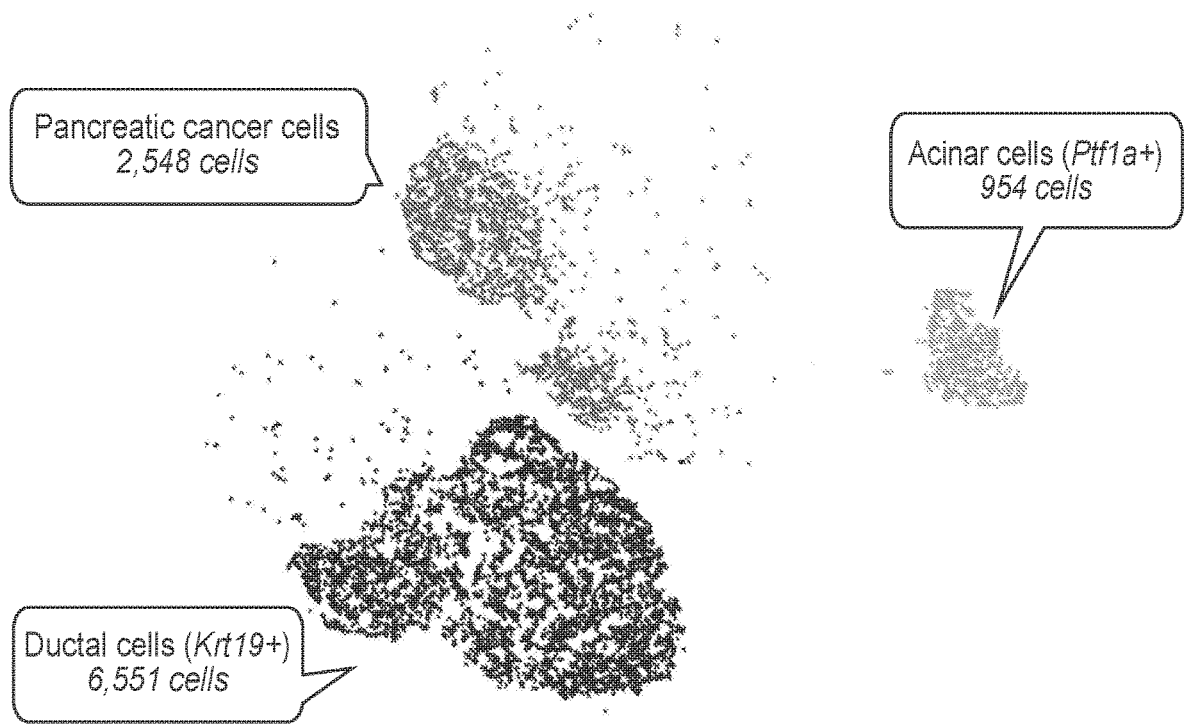
FIG. 2. Molecular profiling of murine pancreatic normal and cancer cells by single-cell RNAseq. Based on transcript-compatibility counts, the 2,548 murine pancreatic cancer cells, 954 murine transformed acinar cells (266-6 cells) and 6,551 murine ductal cells are visualized using t-SNE and colored to label the different cell types.

To understand the gene-expression mediated molecular features of pancreatic normal and cancer cells (FIG. 1), single-cell RNAseq (scRNAseq) analysis was performed on the murine pancreatic cancer cells, murine transformed acinar cells (266-6 cells) and murine ductal cells (FIG. 2). 2,548 murine pancreatic cancer cells, 954 murine transformed acinar cells (266-6 cells) and 6,551 murine ductal cells were collected and analyzed (FIG. 2). The 3 types of cells were then separated based on their transcript-compatibility counts to show distinct molecular profiles, and validated by the expression level of genes including, p53 (lower in the murine pancreatic cancer cells), Krt19 (higher in the pancreatic ductal cells) and Ptf1a (higher in the pancreatic acinar cells).

Example 3: CRISPRi-Mediated Target Suppression and Validation

Figure 3:
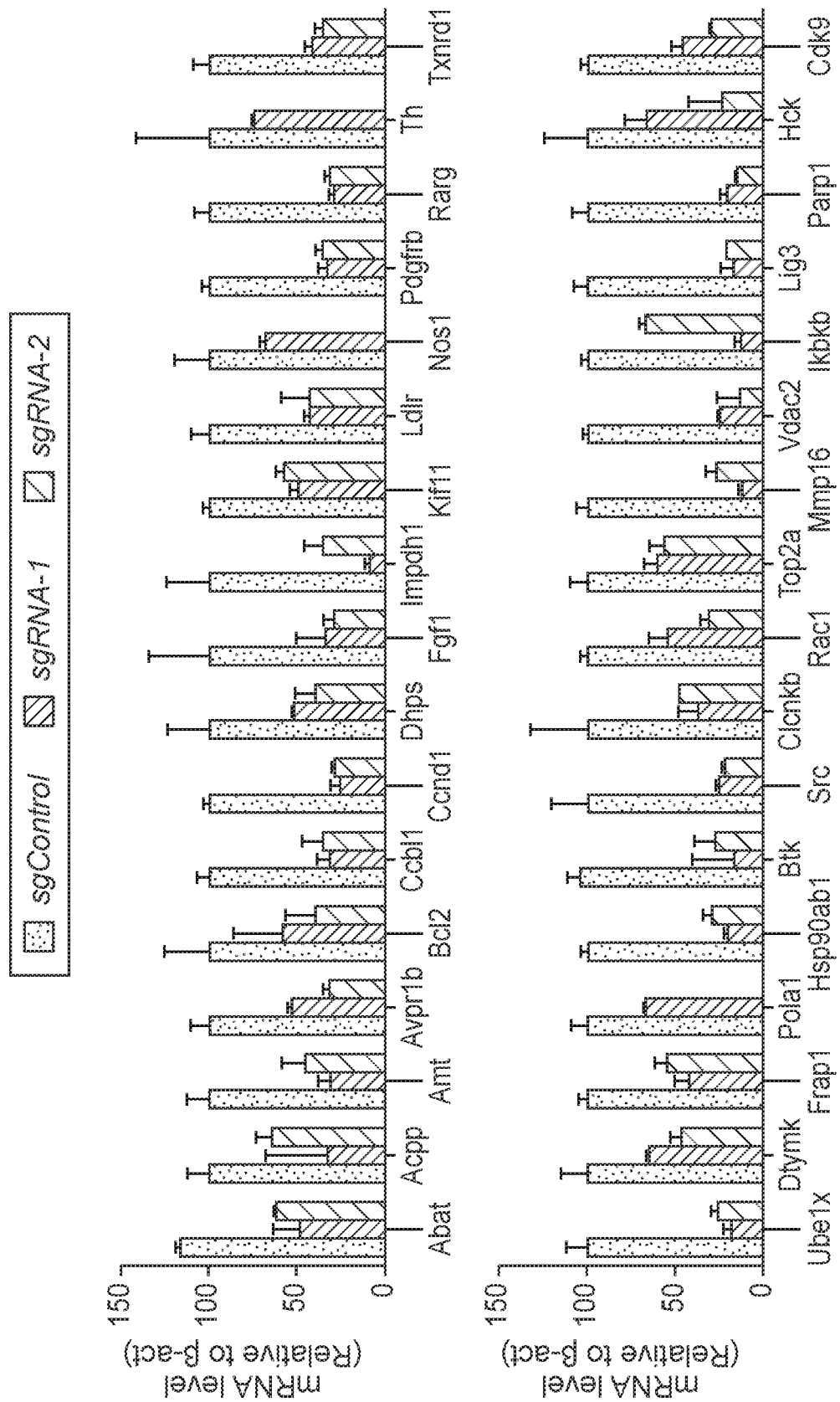
FIG. 3. CRISPRi (CRISPR interference)-mediated suppression of candidate target genes in murine pancreatic cancer cells. The murine pancreatic cancer cells expressing a catalytically dead Cas9 fused to a transcriptional repressor peptide KRAB (dCas9-KRAB) are transduced with BFP-linked sgRNAs targeting candidate genes. Two independent sgRNAs are used. Quantitative PCR (qPCR) analysis of gene expression in murine pancreatic cancer cells are shown on day 5 after sgRNA transduction.
Figure 4B:
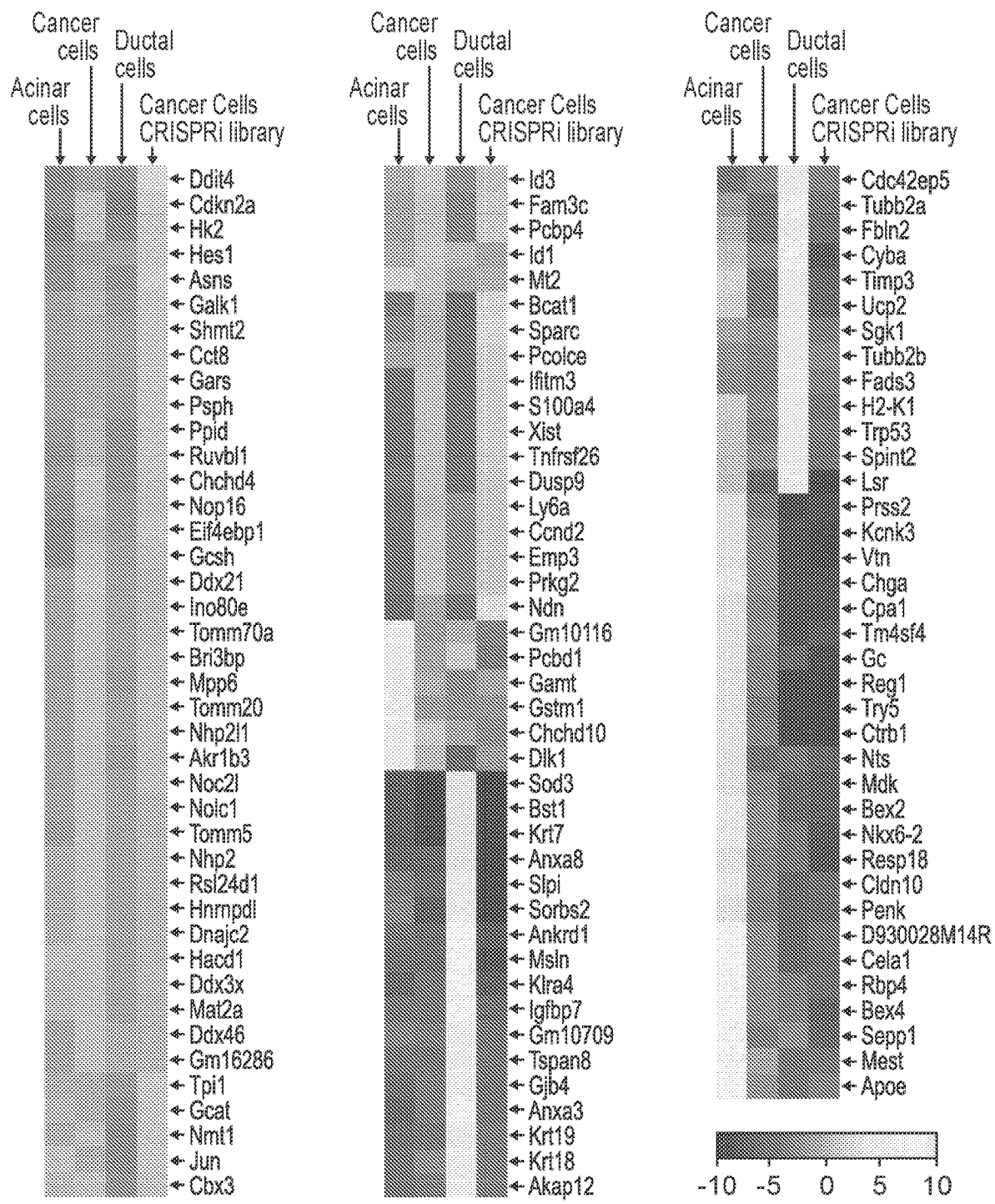
Figure 4C:
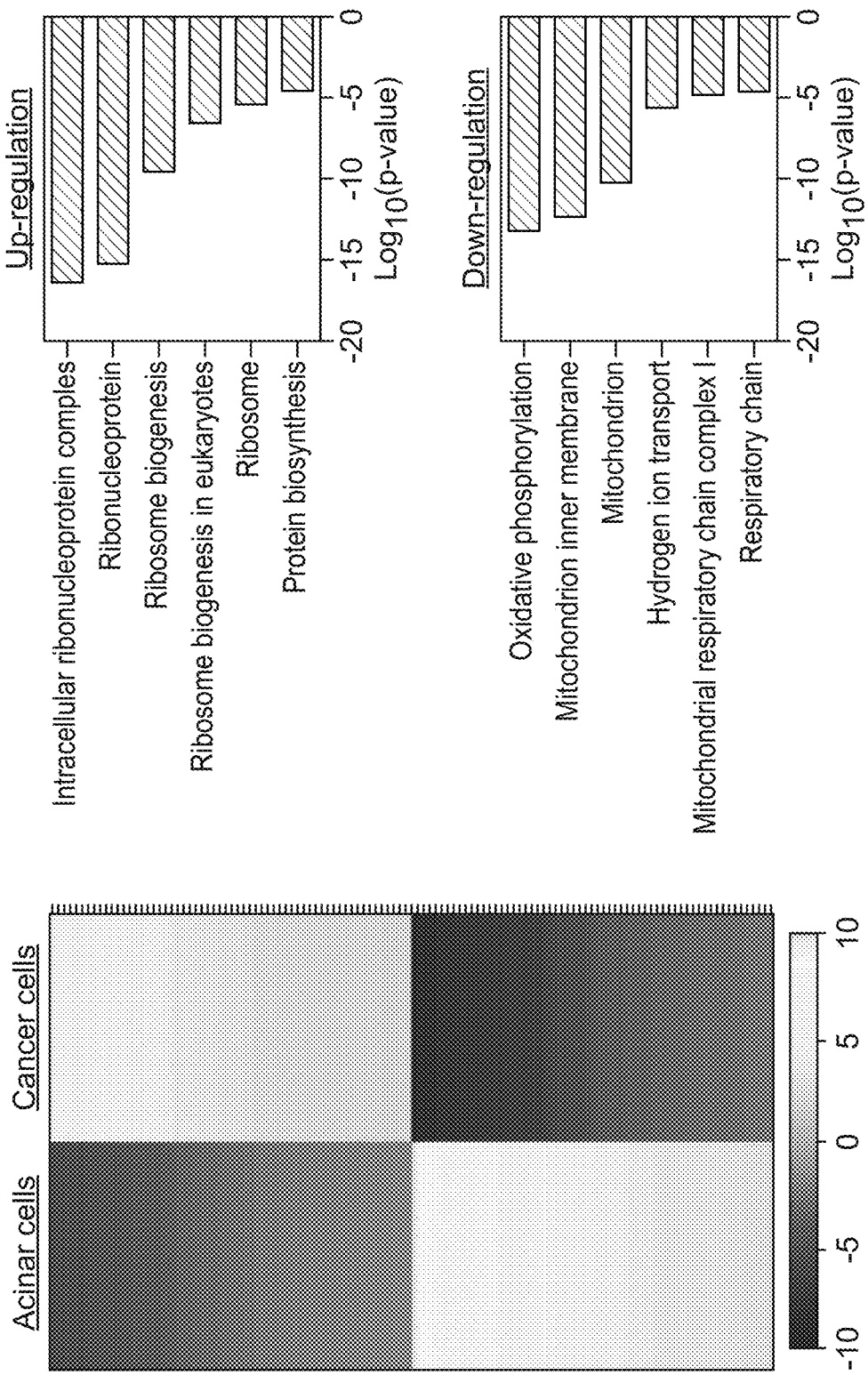
Figure 4D:
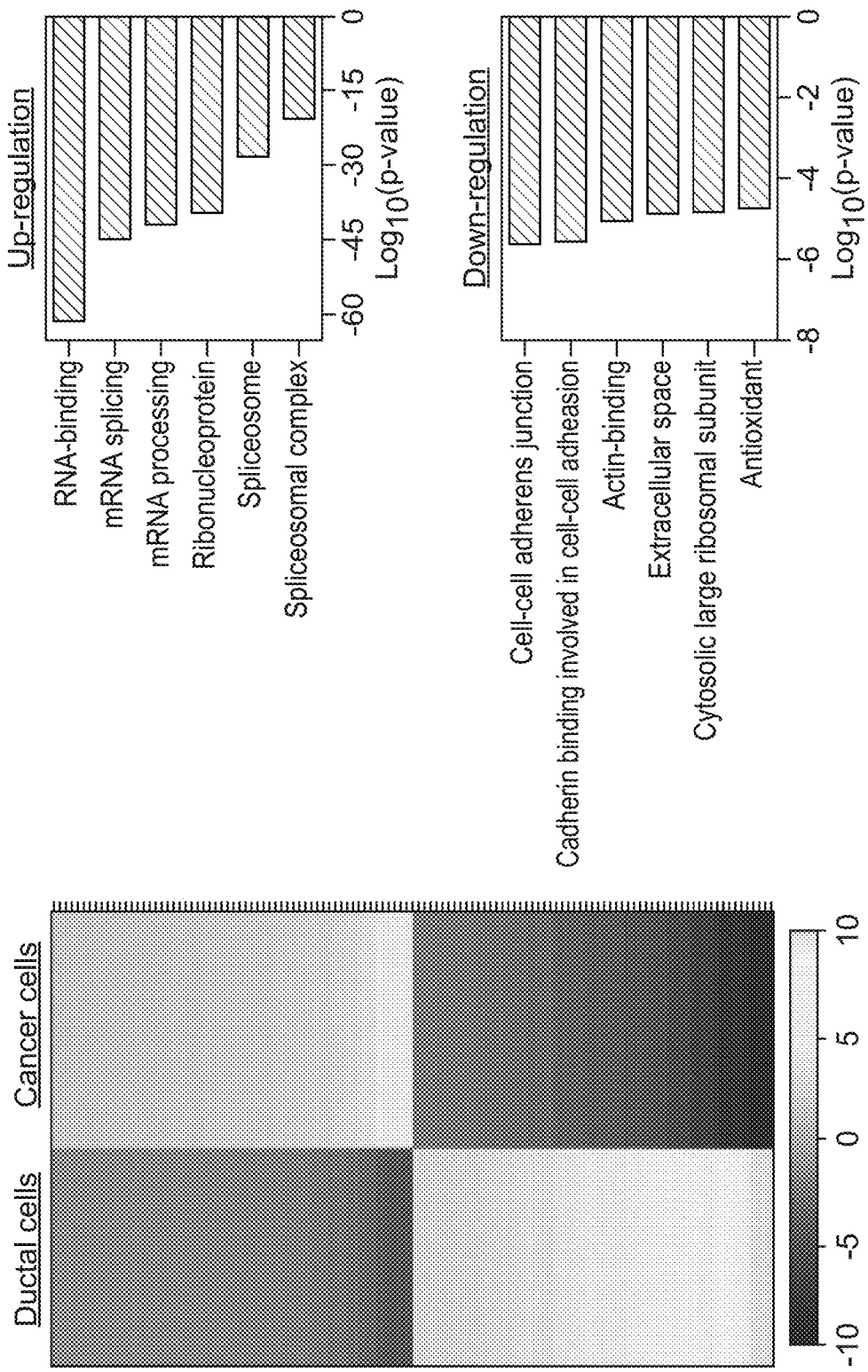
Figure 5:
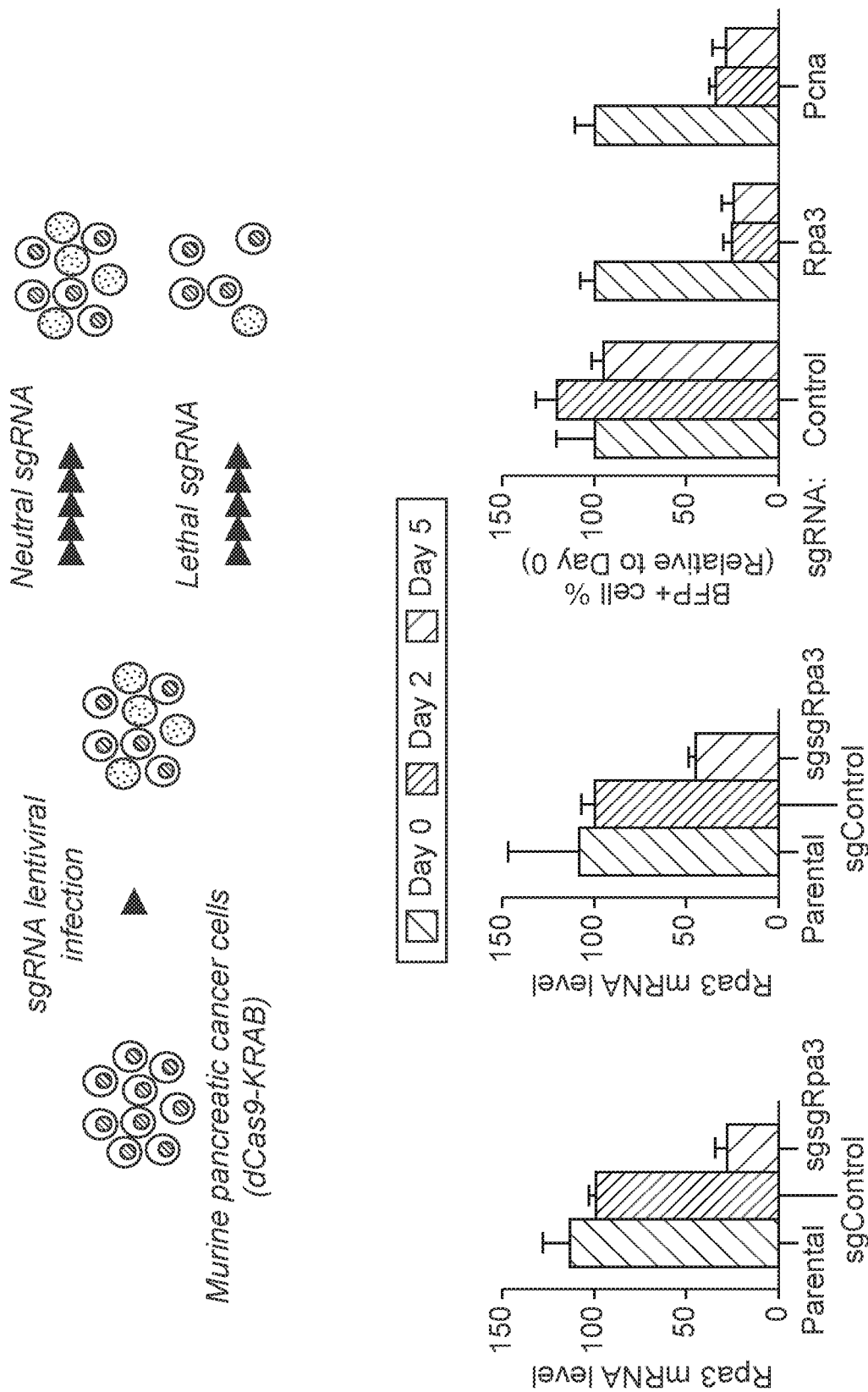
FIG. 5. CRISPRi-mediated validation of candidate target genes in murine pancreatic cancer cells. The murine pancreatic cancer cells expressing a catalytically dead Cas9 fused to a transcriptional repressor peptide KRAB (dCas9-KRAB), are transduced with BFP-linked sgRNAs targeting candidate genes. BFP+ cells were mixed with untransduced cells at around 1:1 ratio and subsequently cultured and the percentage of BFP+ (sgRNA expressing) cells was determined at different time points (results at day 0, day 2 and day 5 are shown and are relative to day 0). Changes were used as readout of the growth inhibitory effects. The graphs show the validation of the control sgRNAs (sgControl, sgRpa3, and sgPcna) in the murine pancreatic cancer cells. Values are mean+SD of three independent experiments.

To identify potential therapeutic targets in pancreatic cancer, a custom CRISPRi library targeting 34 drug target genes was constructed (FIG. 3). For the most of candidate genes, two sgRNAs showing robust suppression of the gene expression were identified (FIG. 3). To study the change of molecular features upon CRISPRi-mediated target suppression, the library lentiviral pool was transduced into the cells (two biological replicates) using conditions that predominantly lead to a single lentiviral integration; and single-cell RNAseq analysis of the cells was performed. 5,997 (biological replicate 1) and 6,272 (biological replicate 2) murine pancreatic cancer cells harboring the CRISPRi library were collected and analyzed (FIG. 4A). Interestingly, the CRISPRi library pancreatic cancer cells were located between the parental murine pancreatic cancer cells and the two other cell types including murine transformed acinar cells (266-6 cells) and murine ductal cells (FIG. 4A). The single-cell RNAseq data can be also used for bulk analysis to identify the genes and pathways related to the three types of pancreatic cells (FIG. 4B; gene list in FIG. 8). To further validate potential candidate targets, a competitive assay can be performed, and can be validated by targeting essential genes such as Rpa3 and Pena (FIG. 5). Together, this result indicates that the platform can be used to identify potential drug target genes by combining CRISPRi-mediated target suppression and single-cell RNAseq-based molecular feature analysis.

Example 4: Cloud Functional Genomics Pipeline, Variational Inference and Downstream Analysis The inference and downstream analysis workflow is depicted in FIG. 6C. The generative model takes as input vector representations of gene expression data from single-cell RNA-seq profiles, and uses variational inference and stochastic optimization for deep neural networks to approximate the parameters that govern the distribution of expression values of each gene in every cell, using a non-linear mapping between observations and a low-dimensional latent space. By doing so, it pools information between similar cells or genes while taking nuisance factors of variation such as batch effects and limited sensitivity into account. The algorithm trains a coupled set of encoder/decoder networks, which attempt to minimally and accurately represent the information content within RNA-seq profiles in a latent, low-dimensional space via non-linear feature reduction. The model is trained such that the networks minimize error in reconstructing full profiles from the low-dimensional encoding, a process mathematically equivalent to retaining maximal differentiation between different profiles in the latent space. In addition to enabling one to conduct differential expression analysis by quantifying and accentuating the differentially expressed genes, the resulting latent space mapping serves as a tool for a plethora of downstream analyses; 1) Classification and Clustering: because the networks are optimized to keep different profiles in the latent space maximally differentiated, encoding a new observation can give us a more precise notion of cell identity over generic clustering methods, which often suffer from significant cluster overlapping. 2) Transition Analysis: the latent space is constructed to be continuous such that an inferred non-linear interpolation between any two sample points in the space also exists in the space. This allows one to map a continuous notion of identity between core representations, for instance, diseased and non-diseased cells, detailing an interpolated and smooth transition between the two states. 3) Synthetic Data Augmentation: because the latent space is truly continuous, a complete gene expression profile could be generated from any given point in the latent space by extrapolating via the tuned decoder network. For instance, one can extrapolate the expression of an observation between two recorded observations, a totally healthy and totally diseased cell to obtain the expression profile of a "half" diseased cell by the definition of the latent space, retaining the underlying expression patterns of the space.

Example 5: Supervised Classification to Discriminate Between Murine Pancreatic Wild-Type Ductal and Cancer Cells In the case of supervised machine learning, the collection of scRNA-seq profiles from unperturbed wild-type ductal and pancreatic cancer cells is combined and split into cell-type-stratified train and test datasets via random indexing. The train dataset comprises on the order of 70% of all profiles, while the test dataset comprises on the order of 30% of all profiles. A supervised machine learning model is then trained for maximal accuracy to discriminate between wild-type ductal versus pancreatic cells based on vector representations of single-cell measurements. Applicable machine learning models include, but are not limited to: Random Forest, Gradient Boosting, logistic and linear regression, and convolutional neural networks (CNNs). Data splitting and model training can readily be performed in open-source packages such as sklearn and TensorFlow in Python or caret in R. For CNNs, a minimal network consisting of an input layer, a convolutional layer with three different filter sizes, a max pooling layer, and an activation layer is constructed in TensorFlow to classify unperturbed cells as wild-type or cancer based on this input representation. An example of supervised classification to discriminate between wild-type and cancer cells is depicted in FIG. 7.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

The patent contains a lengthy sequence listing. A copy of the sequence listing is available in electronic form from the USPTO web site (https://seqdata.uspto.gov/?pageRequest=docDetail&DocID=US12270027B2). An electronic copy of the sequence listing will also be available from the USPTO upon request and payment of the fee set forth in 37 CFR 1.19(b)(3).

What is claimed is:

1. A method comprising:
   (a) introducing into a cancer cell and into a corresponding non-cancer cell of a same cell type as the cancer cell, a clustered regularly interspaced short palindromic repeat (CRISPR)/Cas system comprising:
      i) a CRISPR/Cas effector polypeptide; and
      ii) a CRISPR/Cas guide ribonucleic acid (RNA), or a nucleotide sequence encoding the CRISPR/Cas guide RNA, wherein the CRISPR/Cas guide RNA targets a target gene, thereby producing a modified cancer cell and a modified non-cancer cell, both having reduced expression of the target gene;
   (b) sequencing RNA obtained from the modified cancer cell and the modified non-cancer cell to determine a molecular feature or a phenotype in the modified cancer cell and the modified non-cancer cell, thereby generating RNA sequencing data associated with the molecular feature or phenotype; and
   (c) computer processing the RNA sequencing data associated with the molecular feature or phenotype to determine that the molecular feature or phenotype is indicative of a reduction of cancerous state of the modified cancer cell,
   wherein the determining comprises assessing an extent of transcriptional reversion toward a non-cancer cell expression level as a result of having reduced expression of the target gene.

2. The method of claim 1, wherein the CRISPR/Cas effector polypeptide comprises a fusion protein comprising an enzymatically inactive CRISPR/Cas effector polypeptide and a transcriptional inhibitor.

3. The method of claim 1, wherein the CRISPR/Cas effector polypeptide is enzymatically active, and wherein the CRISPR/Cas system comprises two CRISPR/Cas guide RNAs.

4. The method of claim 1, wherein the non-cancer cell is a non-cancerous pancreatic cell, and wherein the cancer cell is a pancreatic cancer cell.

5. The method of claim 1, wherein the non-cancer cell is a non-cancerous brain cell, and wherein the cancer cell is a brain cancer cell.

6. The method of claim 1, wherein the non-cancer cell is a non-cancerous ovarian cell, and wherein the cancer cell is an ovarian cancer cell.

7. The method of claim 1, wherein the non-cancer cell is a non-cancerous breast cell, and wherein the cancer cell is a breast cancer cell.

8. The method of claim 1, wherein the molecular feature comprises an expression level of an indicator gene in the modified cancer cell and the modified non-cancer cell.

9. The method of claim 1, wherein the sequencing further comprises single-cell RNA sequencing.

10. The method of claim 1, wherein (c) further comprises aligning the RNA sequencing data to a reference genome.

11. The method of claim 1, further comprising comparing the molecular feature or phenotype to a reference molecular feature or phenotype.

12. The method of claim 1, wherein the assessing further comprises using a geometric method to determine a distance between transcriptional profiles of the modified cancer cell and the modified non-cancer cell.

13. The method of claim 1, wherein the assessing further comprises processing gene expressions of the modified cancer cell and the modified non-cancer cell with a trained supervised machine learning classifier to classify the gene expressions as indicative of a cancer cell expression level or a non-cancer cell expression level, wherein the trained supervised machine learning classifier is trained on cancer cell expression data and non-cancer cell expression data.

14. The method of claim 13, wherein the trained supervised machine learning classifier comprises a deep learning classifier, a random forest classifier, a gradient boosted classifier, or a convolutional neural network.

15. The method of claim 14, wherein the deep learning classifier further comprises a variational autoencoder.

16. The method of claim 14, wherein the deep learning classifier further comprises a generative classifier.

17. The method of claim 16, wherein the generative classifier comprises a non-linear mapping between (i) observed expression values of genes in the modified cancer cell and the modified non-cancer cell and (ii) a latent space.

18. The method of claim 17, wherein the latent space is a low-dimensional latent space generated via non-linear feature reduction.

19. The method of claim 13, further comprising performing a dimensionality reduction of the data associated with the molecular feature or phenotype.

20. The method of claim 1, wherein the target gene comprises a plurality of target genes, and wherein (c) further comprises assessing an extent of transcriptional reversion toward a non-cancer cell expression level as a result of having reduced combinatorial expression of the plurality of target genes.

21. The method of claim 1, wherein the target gene is selected from the group consisting of: Ddit4, Cdkn2a, Hk2, Hes1, Asns, Galk1, Shmt2, Cct8, Gars, Psph, Ppid, Ruvbl1, Chchd4, Nop16, Eif4ebpl, Gcsh, Ddx21, Ino80e, Tomm70a, Bri3 bp, Mpp6, Tomm20, Nhp211, Akr1b3, Noc2I, Nolc1, Tomm5, Nhp2, Rsl24d1, Hnrnpdl, Dnajc2, Hacd1, Ddx3x, Matta, Ddx46, Gm16286, Tpil, Gcat, Nmt1, Jun, Cbx3, Id3, Fam3c, Pcbp4, Id1, Mt2, Bcat1, Sparc, Pcolce, Ifitm3, S100a4, Xist, Tnfrsf26, Dusp9, Ly6a, Ccnd2, Emp3, Prkg2, Ndn, and a combination thereof.

22. The method of claim 1, wherein the target gene is selected from the group consisting of: Gm10116, Pcbd1, Gamt, Gstm1, Chchd10, DIk1, Sod3, Bst1, Krt7, Anxa8, Slpi, Sorbs2, Ankrdl, Msln, KIra4, Igfbp7, Gm 10709, Tspan8, Gjb4, Anxa3, Krt19, Krt18, Akap12, Cdc42ep5, Tubb2a, FbIn2, Cyba, Timp3, Ucp2, Sgk1, Tubb2b, Fads3, H2-K1, Trp53, Spint2, Lsr, Prss2, Kcnk3, Vtn, Chga, Cpal, Tm4sf4, Gc, Reg1, Try5, Ctrb1, Nts, Mdk, Bex2, Nkx6-2, Resp18, Cldn10, Penk, D930028M14R, Cela1, Rbp4, Bex4, Sepp1, Mest, Apoe, and a combination thereof.

23. The method of claim 1, wherein the assessing further comprises determining rank-order statistics for genes expressed in the modified cancer cell and the modified non-cancer cell.

24. The method of claim 1, wherein the assessing further comprises performing unsupervised clustering of transcriptional profiles of the modified cancerous cell and the modified non-cancerous cell.

25. The method of claim 1, further comprising identifying the target gene as a target for cancer treatment based at least in part on the determining in (c).

* * * * *